(12) United States Patent
Medintz et al.

(10) Patent No.: US 10,183,080 B2
(45) Date of Patent: Jan. 22, 2019

(54) USE OF SINGLE DENDRITIC WEDGE CELL PENETRATING PEPTIDES TO FACILITATE CELLULAR DELIVERY OF NANOPARTICLES AND NANOPARTICLES CARRYING CARGOS

(71) Applicant: The Government of the United States of America, as represented by the Secretary of the Navy, Washington, DC (US)

(72) Inventors: Igor L. Medintz, Springfield, VA (US); James B. Delehanty, Washington, DC (US); Joyce Breger, Greenbelt, MD (US); Markus Muttenthaler, Brisbane (AU); Philip E. Dawson, San Diego, CA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/694,114

(22) Filed: Sep. 1, 2017

(65) Prior Publication Data
US 2018/0071399 A1    Mar. 15, 2018

Related U.S. Application Data

(60) Provisional application No. 62/382,820, filed on Sep. 2, 2016.

(51) Int. Cl.
*A61K 38/08* (2006.01)
*A61K 47/64* (2017.01)
*A61K 47/69* (2017.01)
*A61K 31/704* (2006.01)
*A61K 47/52* (2017.01)
*A61K 47/62* (2017.01)

(52) U.S. Cl.
CPC .......... *A61K 47/641* (2017.08); *A61K 31/704* (2013.01); *A61K 38/08* (2013.01); *A61K 47/52* (2017.08); *A61K 47/62* (2017.08); *A61K 47/645* (2017.08); *A61K 47/6923* (2017.08); *A61K 47/6929* (2017.08)

(58) Field of Classification Search
None
See application file for complete search history.

(56) References Cited

U.S. PATENT DOCUMENTS

2015/0297742 A1    10/2015   Strieker et al.

OTHER PUBLICATIONS

Breger et al. "Nanoparticle cellular uptake by dendritic wedge peptides: achieving single peptide facilitated delivery" Nanoscale, 2017, 9, 10447-10464.

*Primary Examiner* — Lianko G Garyu
(74) *Attorney, Agent, or Firm* — US Naval Research Laboratory; Roy Roberts

(57) ABSTRACT

Nanoparticles (and optionally a cargo such as a drug) can be delivered to cells by attaching just a single dendritic peptide to the nanoparticle. The dendritic peptide includes a polyhisitidine motif and a hinge and a spacer connecting the polyhistidine to a lysine-based dendritic wedge displaying at least two copies of a cell-penetrating peptide motif.

6 Claims, 12 Drawing Sheets
(3 of 12 Drawing Sheet(s) Filed in Color)
Specification includes a Sequence Listing.

```
                        SEQUENCE LISTING

<160> NUMBER OF SEQ ID NOS: 5

<210> SEQ ID NO 1
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (12)..(13)
<223> OTHER INFORMATION: oxime bond and hexamine spacer

<400> SEQUENCE: 1

Arg Arg Arg Arg Arg Arg Arg Arg Arg Phe Gly Trp Pro Pro Pro Pro
1               5                   10                  15

Pro Pro Pro Pro Pro Gly Gly His His His His His His
            20                  25

<210> SEQ ID NO 2
<211> LENGTH: 11
<212> TYPE: PRT
<213> ORGANISM: Artificial Sequence
<220> FEATURE:
<223> OTHER INFORMATION: synthetic construct

<400> SEQUENCE: 2

Arg Arg Arg Arg Arg Arg Arg Arg Arg Phe Gly
1               5                   10

<210> SEQ ID NO 3
<211> LENGTH: 11
<212> TYPE: PRT
<213> ORGANISM: Artificial Sequence
<220> FEATURE:
<223> OTHER INFORMATION: synthetic construct

<400> SEQUENCE: 3

His His His His His His Gly Gly Pro Pro Trp
1               5                   10

<210> SEQ ID NO 4
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (15)..(16)
<223> OTHER INFORMATION: hydrazine bond
<220> FEATURE:
<221> NAME/KEY: SITE
<222> LOCATION: (31)..(31)
<223> OTHER INFORMATION: amide blocking the C-terminal carboxyl

<400> SEQUENCE: 4

His His His His His His Ser Leu Gly Ala Ala Ala Gly Ser Gly Lys
1               5                   10                  15
```

```
Ser Ser Thr Gly Gly Gln Asn Gly Glu Asp Thr Gly Thr Ser Cys
        20                  25                  30
```

<210> SEQ ID NO 5
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (15)..(15)
<223> OTHER INFORMATION: amidation

<400> SEQUENCE: 5

```
Gly Ser Gly Ala Ala Ala Gly Leu Ser His His His His His His
1               5                   10                  15
```

USE OF SINGLE DENDRITIC WEDGE CELL PENETRATING PEPTIDES TO FACILITATE CELLULAR DELIVERY OF NANOPARTICLES AND NANOPARTICLES CARRYING CARGOS

CROSS-REFERENCE TO RELATED APPLICATIONS

This Application claims the benefit of U.S. Provisional Application 62/382,820 filed on Sep. 2, 2017, the entirety of which is incorporated herein by reference.

BACKGROUND

A majority of current drug therapies are delivered systemically and treat the whole body even when disease is confined to a specific organ or tissue type; this increases the required dosage while causing unwanted side effects such as offsite or systemic toxicity. Further, maintaining a therapeutic dose can be difficult when drugs are quickly metabolized or poorly soluble. Achieving a therapeutic dose with conventional medication over an appropriate time frame requires taking multiple doses, resulting in increased cost and often decreasing compliance from patients. Nanoparticle mediated drug delivery (NMDD) has the potential to address many of these shortcomings. Nanoparticles have high surface area-to-volume (S/V) ratios allowing for a relatively large drug cargo carrying/display capacity to be achieved with relatively few particles. Improved pharmacokinetics from smaller dosages can be accessed from the enhanced permeability and retention (EPR) effect in the case of tumors or if a targeted, localized, and controlled drug delivery can be incorporated into the same platform. Another exciting aspect of NMDD is the possibility of creating truly "theranostic" nanomaterials. These multimodal devices have may allow for simultaneous monitoring of disease while also allowing for targeted, stimuli-responsive release of poorly soluble drugs. Although potentially transformative, the development of NMDD and related theranostic devices still requires solving a plethora of issues ranging from the initial bioconjugation chemistry used to assemble the structures to accurate targeting and then final clearance from the body and this, in turn, is providing many fertile avenues of research.

A significant effort in developing NPs for biological applications has been in facilitating directed cellular uptake. Although a number of chemical and physical methods are available, for example, use of Lipofectamine or electroporation, one of the most popular methods to achieve cellular uptake still remains the use of cell penetrating peptides (CPPs). These are predominantly based on truncated versions of the TAT peptide derived from the HIV-1 trans-activating regulatory protein and typically contain consecutive repeats of positively charged lysine or arginine residues. Such polycationic peptides have facilitated intracellular delivery of cargo such as drugs, NPs, small chemical molecules, and even large DNA fragments that would otherwise not enter the cell. Although some debate continues, the mechanism by which CPPs accomplish cellular uptake is generally agreed upon. The localized CPP positive charge initially associates with the negatively-charged heparan sulfate proteoglycan (HSPG) of the cellular membrane or similar molecules of the glycocalyx allowing for subsequent collection into nascent endosomes which then transport the attached cargo into the cytosol. The vast majority of materials taken up in this manner remain sequestered within the endolysosomol system, unless a given component or cargo has innate membrane crossing or endosomal escape properties by being lipidic, lipophilic, amphipathic or the like. In terms of specific NP delivery, CPPs have mediated cellular delivery of a myriad of NP types ranging from gold NPs and semiconductor quantum dots (QDs) to softer dendrimers and polymersomes. CPPs, which are generally <3 kDa, have even mediated cellular uptake of QDs decorated with over a 1,000 kDa of protein cargo in the form of a macromolecular light harvesting complex. Significant resources continue to be invested to improve CPP-mediated NP delivery including optimizing given sequences, selecting for new motifs, imbuing them with endosomal escape properties, and providing them with organelle-specific delivery properties.

An important factor that is often not appreciated about CPP mediated cellular delivery of almost every type of NP material is that it requires a significant amount of CPP to be decorated around the NP surface in order for uptake to occur efficiently; i.e., high avidity over a short exposure time with significant intracellular accumulation. Typical ratios utilized can range from 10 to 20 CPPs per NP or even higher. The net result is that a significant portion of a given NP's surface area and especially their cargo-carrying capacity may be given over to accomplish this by directed CPP attachment to the NP surface or its peripheral chemical groups. As opposed to relying on multiple copies of a given peptidyl motif or other targeting molecule to achieve effective cellular targeting or uptake, there is a growing literature describing how displaying multivalent versions of cellular binding moieties or CPPs can significantly increase initial cellular binding and subsequent cellular uptake. For example, Grillaud and coworkers showed that high cellular uptake of a series of polycationic adamantane-based dendrons was dependent upon the synthetic generation number. Gray et al. showed that functionalizing liposomes with specific phage-display derived tetrameric peptides increased targeting to a biomarker displayed on human 112009 lung adenocarcinoma cells. The Neundorf Lab demonstrated that dimerization of a novel CPP derived from an antimicrobial protein resulted in enhanced cellular uptake and drug delivery.

As NMDD, theranostics, and a variety of NP-related technologies mature into biological applications, it is critical to optimize their design parameters and especially their cargo carrying and surface display capabilities. A need exists for improved delivery of nanoparticles.

BRIEF SUMMARY

CPPs have recently attracted significant attention due to increasing interest in their use for NP mediated delivery. CPPs based on consecutive repeats of positively charge arginine facilitate cellular uptake by interacting with negatively charged moieties on the cell surface, instigating endocytosis. To achieve efficient NP cellular uptake, 10 to 20 CPPs or more are often needed, limiting the available NP surface area for other therapeutic cargo to be attached. In past research efforts, modular peptides have been synthesized that contain specific intracellular functions, such as organelle specific targeting and/or endosomal escape, with facile NP attachement chemistry in the form of a ($His_6$). The ($His_6$) tag of these peptides enables rapid self-assembly to the NP surface through metal affinity binding, for example. Currently, a series of modular peptides with a ($His_6$) tag based on a dendritic wedge have been synthesized to display increasing branches of $(Arg_9)_n$ where n=1×, 2×, 4×, 8×, or 16× for enhanced NP cellular uptake. An innovative oxime ligation strategy was utilized to attach up to 16 branches of (Arg$_9$) to a lysine based dendritic scaffold. Each dendritic wedge peptide contains a Pro$_9$ spacer sequence which extends the rest of peptide away from the NP surface, ensuring optimal display of the (Arg$_9$)$_{n=1-16}$ branches. The characteristics of each dendrimeric peptide are summarized in Table 1. By utilizing a dendritic wedge based peptide that displays multiple copies of (Arg$_9$), NP surface area is freed for the attachment of cargo while still maintaining efficient cellular delivery.

Significantly, this provides the ability to achieve NP cellular uptake with single dendritic peptide with as few as two (Arg$_9$) branches after a short incubation period of 30 minutes, as well as the ability to deliver >600 kDa protein cargo per NP to cells with only one dendritic wedge peptide and an incubation time of 1 hr.

Aspects of this work are described in *Nanoscale*, 2017, 9, 10447-10464.

In one embodiment, a method of delivering a nanoparticle to a cell includes contacting a living cell with a nanoparticle bound to a single dendritic peptide thereby causing entry of the nanoparticle into the cell, wherein the dendritic peptide has a polyhisitidine motif and a hinge and a spacer connecting the polyhistidine to a lysine-based dendritic wedge displaying at least two copies of the peptide sequence RRRRRRRRRFG (SEQ ID No: 2).

In further embodiments, the nanoparticle is also bound to a cargo which is carried into the cell along with the nanoparticle.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows an overview of peptide dendrimer synthesis. The precursor peptides (functional peptide with amino-oxy group and dendritic scaffold peptide with N-terminal serine residues) are produced by solid phase synthetic peptide synthesis (SPPS). The N-terminal serine-residues are chemoselectively converted with NaIO$_4$ into aldehydes, which are then reacted with the amino-oxy group of the functional peptide to form the desired peptide dendrimers. This oxime ligation is catalyzed by aniline. The significant size difference between the precursor peptides and the final dendrimer product allows for centrifugal size-exclusion purification. FIG. 1B shows coordination of peptide dendrimers to PEGylated QDs. Schematic representation of the designed and assembled peptide ligands, their functional subunits and how they assemble to the surface of 550 nm DHLA-PEG$_{750}$-OMe QDs through metal coordination between the Zn$^{+2}$ rich surface and the peptidyl His$_6$ tag. The DHLA ligand is shown in the thioctic acid form.

FIG. 3A is a representative TEM micrograph of the 550 nm CdSe/ZnS QD with an average size of 4.7±0.4 nm. Inset shows a single QD with a 5 nm size bar. FIG. 3B is a plot of the hydrodynamic diameters of QD-peptide assemblies (circles, left axis) and their diffusion coefficients (triangles, right axis) as (Arg$_9$)$_n$ increases from dynamic light scattering (DLS) analysis. Ratios of 5 peptides per QD was utilized for these measurements. FIGS. 3C-3E show the estimated association constants ($k_a$), dissociation constants ($k_d$), and binding constants ($K_D$, where $K_D=k_d/k_a$), respectively, for dendritic peptide assembled QD interactions with a heparan proteoglycan sulfate surface as monitored with SPR analysis. Ratios of peptides per QD was utilized for the SPR experiments are indicated in each panel. Values of 20 were used to achieve maximal packing in all cases except that of the (Arg$_9$)$_{16}$ where there may be some excess free peptide. Values not shown are below the scale of the plots in FIGS. 3C-3E.

FIG. 5A shows COS-1 cells that were incubated in the presence of the dendritic peptide-QD bioconjugates from 30 min to 24 h. After only 30 min, QD uptake become visible for the QD-(Arg$_9$)$_2$ conjugates. As (Arg$_9$)$_n$ increases, the accumulation of endosomal QDs also increases. Similarly, as exposure time becomes longer, the accumulation of QDs intracellularly increases for each dendritic peptide. FIG. 5B shows fluorescence intensity per cell extracted from the representative images in FIG. 5A. Values not shown are below scale. FIG. 5C shows the averaged fraction of endosomes positive for QD staining per cell after 1 h incubation.

FIG. 6A shows the averaged number of endosomes per cell. FIG. 6B shows the average total endosomal area based on pixels identified by the software within a defined area delineated in each image. FIG. 6C shows integrated endosomal intensity

FIG. 8B has representative micrographs showing $(Arg_9)_8$-mediated delivery of QDs with selected cargos including a Cy5-labeled peptide (Cy5 peptide, ratio=30/QD), a doxorubicin-labeled peptide (Dox peptide, ratio 25/QD), and mCherry fluorescent protein (ratio=30/QD); $(Arg_9)_8$-ratios were 1, 0.5, and 1 per QD while cellular exposure times were 2, 1, and 1 h, respectively. QD PL is green, nuclei stained with DAPI are in blue, Cy5, Dox and mCherry cargos are colored red. Yellow indicates colocalization of QD and cargo (red+green).

DETAILED DESCRIPTION

Definitions

Figure 1A:
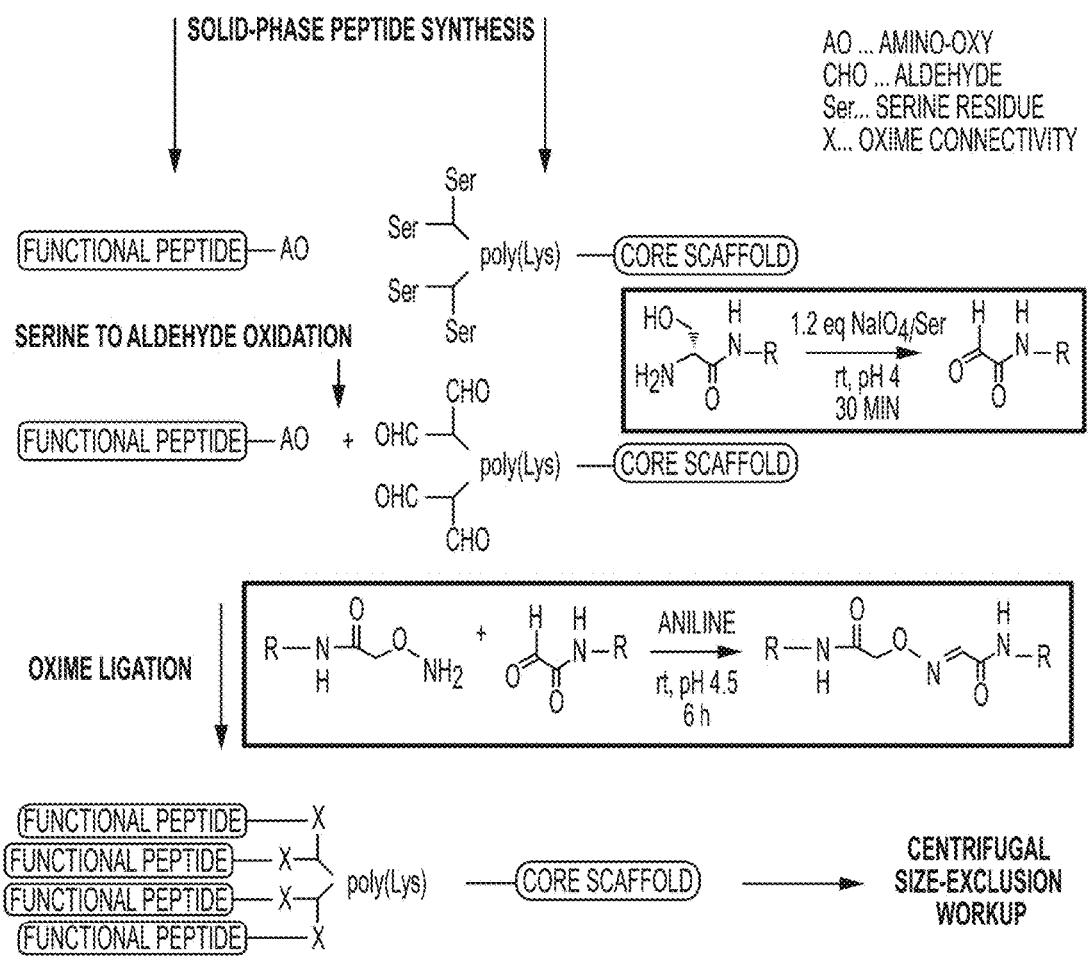
FIGS. 1A and 1B illustrate a synthetic strategy for dendritic peptide assembly and coordination to PEGylated QDs.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

The term "quantum dot" or "QD" as used herein refers to an inorganic semiconductor crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). QDs are characterized by their substantially uniform nanometer size, frequently exhibiting approximately a 10% to 15% polydispersion or range in size.

A QD is capable of emitting electromagnetic radiation upon excitation (i.e., the QD is photoluminescent) and includes a "core" of one or more first semiconductor materials, and may be surrounded by a "shell" of a second semiconductor material. A QD core surrounded by a semiconductor shell is referred to as a "core/shell" QD. The surrounding "shell" material will preferably have a bandgap energy that is larger than the bandgap energy of the core material and may be chosen to have an atomic spacing close to that of the "core" substrate.

The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbS, PbSe, and an alloy or a mixture thereof. Preferred shell materials include ZnS.

A QD is optionally surrounded by a "coat" of an organic capping agent. The organic capping agent may be any number of materials, but has an affinity for the QD surface. In general, the capping agent can be an isolated organic molecule, a polymer (or a monomer for a polymerization reaction), an inorganic complex, or an extended crystalline structure. The coat can be used to convey solubility, e.g., the ability to disperse a coated QD homogeneously into a chosen solvent, functionality, binding properties, or the like. In addition, the coat can be used to tailor the optical properties of the QD. Thus, the quantum dots Springfield-Branson National Airportherein include a coated core, as well as a core/shell QD.

The term "nanoparticle" as used herein includes the above-mentioned QDs in addition to other nano-scale and smaller particles. A nanoparticle has a size of less than about 1 micron, optionally less than about 900, 800, 700, 600, 500, 400, 300, 100, 80, 60, 50, 40, 30, 20, 10, 9, 8, 7, 6, 5, 4, 3, 2, or 1 nanometers. A nanoparticle may have various shapes such as a rod, a tube, a sphere, and the like. Nanoparticles may be made from various materials including metals, carbon (such as carbon nanotubes), polymers, and combinations thereof.

Overview

Nanoparticle mediated drug delivery can help overcome many limitations associated with traditional systemic drug administration. As such, significant efforts are currently being invested in optimizing the drug cargo carrying capacity and cellular delivery efficiency of this potential new class of therapeutics. As described herein, multivalent cell penetrating peptide (CPP) dendrimers facilitate rapid and efficient cellular delivery of semiconductor quantum dots (QDs). This indicates a role for such CPP dendrimers in nanoparticle mediated drug delivery.

One possible avenue that may accomplish this is to develop and utilize far more potent CPPs such that efficient cellular uptake can still be accomplished while requiring significantly fewer peptide copies to be displayed on the NP. The ultimate goal would be to only require the use of a single peptidyl entity per NP to achieve cellular delivery. This describes the synthesis of a series of modular, branched dendritic peptides that display increasing numbers of polyarginine CPP motifs in pursuit of enhancing NP cellular uptake while simultaneously reducing the overall number of discrete peptide entities required. The modular, multivalent CPP structure was assembled using chemoselective oxime ligation and incorporated sequential generations of a lysine-based dendrimeric architecture (see FIG. 1A). As a prototypical nanoparticulate material, semiconductor quantum dots (QDs) were used as they are easily visualized in cells due to their strong photoluminescence (PL), are relatively homogeneous in size, and, more importantly, provide access to facile peptide bioconjugation while maintaining control over the ratio of CPP per QD. Following preliminary physicochemical characterization of the QD-CPP bioconjugates, QD cellular delivery kinetics was investigated as a function of QD-CPP exposure time and assembly ratio per QD. The results confirm that single copies of these multivalent CPPs can indeed facilitate delivery of QDs and QDs decorated with various cargo to cells in a non-toxic manner.

The modular multivalent CPP dendrimers were assembled through a convergent oxime ligation strategy between $(Arg_9)_n$ CPP motifs and a dendritic QD coordination scaffold. The final dendrimeric peptides included a terminal hexa-histidine motif for metal-affinity binding to QDs and a $Pro_9$ spacer followed by a branching poly-lysine scaffold for the intended multivalent wedged display of the $(Arg_9)_n$ binding motif with n=1×, 2×, 4×, 8×, 16× multivalency. QD surface display capability for each of these dendrimeric CPP was first estimated using in silico structural simulations. QD-$(Arg_9)_{1-16}$ conjugates were then characterized by dynamic light scattering, and surface plasmon resonance-based binding assays to heparan sulfate proteoglycan surfaces. QD cellular uptake via endocytosis for the peptides was confirmed and delivery kinetics investigated as a function of QD-$(Arg_9)_{1-16}$ conjugate exposure time and assembly ratio per QD. The ability of single peptide conjugates to the predicted net charge at pH 7.4. Each of the motifs incorporated into these modular peptides along with their relative positioning in the sequence are meant to impart different properties to the final construct. For example, the terminal $His_6$ provides for self-assembly to the QD surface as discussed below. Other lengths of poly-histidine sequence are also expected to function similarly. The $Gly_2$ is meant to be flexible, allowing the peptide to bend away from the QD surface and extend out from the surrounding PEG layer—other peptides and/or other lengths could serve this purpose. The Trp residue provides a means to quantitate the peptide using UV absorption and could be omitted in some embodiments. The $Pro_9$ is meant to assume a rigid type II helix and act as a spacer extending the rest of the peptide through the QDs PEG layer. Other proline sequence lengths, for example of from 6 to 12 residues, might also provide this function. The hexamine spacers have a similar function and are used to extend the peptide chains of the 1× and 2× ligands, which do not have the same type of core poly(lysine) sequence. Nonsymmetric dendritic branching (2×, 4×, 8×, 16×) is achieved through the use of poly(lysine) dendritic wedges. Finally, the peptides display 1, 2, 4, 8 or 16 copies of the cell-penetrating nona-arginine TAT motif (RRRRRRRRRFG which is SEQ ID NO: 2) at the terminus opposite to the $His_6$ QD assembly motif. The unbranched sequence (with a single copy of the cell-penetrating motif) has SEQ ID NO: 1. Overall, this modular design affords the peptide series the ability to assemble to QDs in the same manner with the same relative orientation.

TABLE 1

Selected Properties of the Dendritic Peptides

| $(Arg_9)_n$ | Generation | Sequence (N-C terminus) | MW (Da) | # of Arg | Predicted Charge[1] | Estimated Max/QD | $H_D$ (nm) |
|---|---|---|---|---|---|---|---|
| 1 | 0 | [RRRRRRRRRFG]-x-hex-hex-WP$_9$G$_2$H$_6$ | 3980 | 9 | 9.5 / 8.8 | 41 | (24.3 ± 1.0)[2] 26.7 ± 1.3 |
| 2 | 1 | [(RRRRRRRRRFG)-x-hex-P$_9$G]$_2$-K'WGH$_6$ | 6777 | 18 | 19.5 / 17.8 | 41 | 30 ± 1.4 |
| 4 | 2 | [RRRRRRRRRFG]$_4$-x-K'K'WP$_9$G$_2$H$_6$ | 9355 | 36 | 38.5 / 35.8 | 31 | 30.7 ± 2.0 |
| 8 | 3 | [RRRRRRRRRFG]$_8$-x-K'K'K'WP$_9$G$_2$H$_6$ | 16822 | 72 | 75.5 / 71.8 | 21 | 30.9 ± 1.4 |
| 16 | 4 | [RRRRRRRRRFG]$_{16}$-x-K'K'K'K'WP$_9$G$_2$H$_6$ x = oxime bond hex = hexamine spacer | 31767 | 144 | 139.5 / 143.8 | 11 | 32.7 ± 4.9 |

[1]Full peptide / Arg$_n$ at pH = 7.4 (estimated). [2]Value of QD alone.

effectively facilitate QD uptake into cells was confirmed for the QD-$(Arg_9)_{2-16}$ repeats along with the ability to deliver >600 kDa of protein cargo per QD. Cellular viability assays confirmed minimal to no cytotoxicity for assembly ratios of five peptides per QD using a 1 hour exposure time. Minimizing the number of CPPs required for targeting or cellular uptake is critical for creating the most efficient therapeutic design. This will, in turn, extend the cargo carrying capacity of these composite materials and, more importantly, can allow for additional inclusion of sensors, therapeutics and contrast agents when creating multipurpose theranostic nanoparticle vehicles.

Results

Design and Chemical Synthesis of Poly(Arg)$_{1-16}$ Peptide Dendrimers.

Table 1 lists selected properties of the dendritic peptide series utilized here including their sequence, molecular weight (MW), the number of Arg residues incorporated, and Some of the larger peptide dendrimers approach the size of proteins and are not well suited for assembly by standard linear solid phase peptide synthesis (SPPS). For example, the 16× peptide dendrimer comprises 225 amino acids with a MW of 31.8 kDa. For comparison this is actually larger than yellow fluorescent protein (~27 kDa), multiple copies of which were previously delivered as a QD attached cargo to cells via standard TAT CPPs. To facilitate chemical synthesis, an assembly strategy was devised that is quantitative and chemoselective based on the aniline-catalyzed oxime reaction between aldehydes and amino-oxy groups to ligate purified and unprotected peptide building blocks together (FIG. 1A). The core peptides comprised the $His_6$ QD assembly motif, the poly-proline-II-$Pro_9$ motif, Gly and hexane spacers, Trp and the poly(lysine) branching motif, and were assembled by automated Boc-SPPS. The N-termini were equipped with serine residues that could be selectively oxidized to N-terminal aldehydes with NaIO$_4$ after cleavage from the resin. The core peptides were purified by reverse phase high performance liquid chromatography (RP-HPLC) to >95% purity. The poly-Arg$_9$ TAT motif was also synthesized by automated Boc-SPPS, displaying an amino-oxy group at the N-terminus (amino-oxy-GFR$_9$—NH$_2$), cleaved from the resin by HF, and purified to >95% purity by RP-HPLC. The amino-oxy-poly(Arg)$_9$ peptides were then ligated to the individual aldehyde-core peptides to form the desired 1×, 2×, 4×, 8× and 16× poly(Arg)$_9$ peptide dendrimers. Oxime ligation occurred with 100 mM aniline catalyst in acetate buffer pH 4.5 at room temperature. Ligations were quantitative (driven by a 1.5 eq excess of poly-Arg$_9$ peptide) and complete within 4 h. No incomplete ligation products were observed. Purification was achieved with size-exclusion centrifugal filter membranes (3, 5 and 10 kDa; except for the 1× monomeric ligand, which was purified by RP-HPLC) that efficiently separated the small linear building blocks and salts from the larger peptide dendrimers with good yields (70-90%).

Quantum Dots and Dendritic Poly(Arg)$_{1-16}$ Peptide Bioconjugation.

Luminescent semiconductor QDs served as prototypical nanoparticulate material for cellular delivery. It is expected the quantum dots could be replaced by other nanoparticles with the dendritic peptides attached thereto.

QD nanocrystals provide several inherent properties that enable the experimental design. Along with low polydispersity (<10%) and physicochemical stability, their high quantum yields and stable photoluminescence (PL) allow for long-term cellular tracking studies. The 550 nm emitting CdSe/ZnS core/shell QDs utilized here are made colloidally stable using poly(ethylene glycol) appended dihydrolipoic acid that terminate in a methoxy group (DHLA-PEG-OMe, PEG MW~750 corresponding to n~15 ethylene glycol repeats). QDs surface functionalized with these ligands do not typically aggregate and are stable across a wide range of pH and ion concentrations and their ability to undergo peptide-mediated cellular uptake in a non-toxic manner has been repeatedly verified. Lastly, and perhaps most critical for the current study, polyhistidine-(His$_n$) appended peptides can be controllably conjugated to these QDs using a metal-affinity coordination based self-assembly chemistry. This rapid, facile process typically requires only mixing of the His$_n$-peptides with the QDs at the desired concentrations and relative molar ratios with no subsequent purification needed prior to use in most cases.

As this bioconjugation reaction is inherently a self-assembly process, the actual ratio or valence of peptide to QD can be described by a classical Poisson distribution process:

$$P(n)=(e^{-N}N^n)/n!$$ (Eq. 1)

where P(n) designates the QD population conjugated to exactly n peptides and N is the average peptide/QD ratio. This, of course, assumes that the surface of the QD is not saturated and that each peptide assembles to the QD independently from the next. When reduced to practice, at valencies >4/QD the number of peptides assembled per QD will be a narrow Gaussian distribution with a maximum value centered at the target ratio. To achieve monovalent or single QD labeling with peptides, an assembly ratio of 0.5 peptides/QD is utilized as this results in two species present in the ensemble: those with no peptides (~50%) and those with 1 peptide per QD (~50%). This description has been repeatedly verified experimentally, and is implemented here to evaluate QD single peptide labeling uptake capabilities.

Characterization of Quantum Dot-Poly(Arg)$_{1-16}$ Bioconjugates.

Figure 2A:
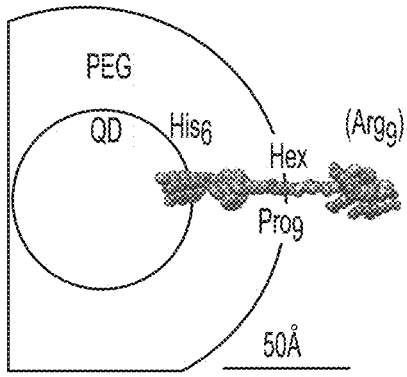
FIGS. 2A-2E show simulations the spatial arrangement of single dendritic peptides attached to QDs. Simulation of each of the dendritic peptides as attached to the 550 nm DHLA-PEG$_{750}$-OMe QDs via the terminal His$_6$ tag. The CdSe/ZnS core/shell QDs are represented by an circle with the surrounding PEG ligand extending another ~3.3 nm. The His$_6$ sequence should be in contact with the QD surface, not contributing to the lateral extension away from the QD. This is followed by a hexamine spacer and the Pro$_9$ motif which is shown here in a type II helix; this serves to extend the rest of the dendritic peptide away from the QD surface. The poly-arginine (Arg$_9$) branches extend outside the PEG layer suggesting availability to interact with the cell surface. The numbers in white (lower right) indicate the dendrimer generation number while the blue (Arg$_9$)$_n$ indicates the number of (Arg$_9$) copies (1, 2, 4, 8, 16) present. The simulation indicates that at the higher degrees of dendrimer branching there could be steric hindrance between peptides at higher assembly ratios per QD. Simulation to scale.
Figure 2B:
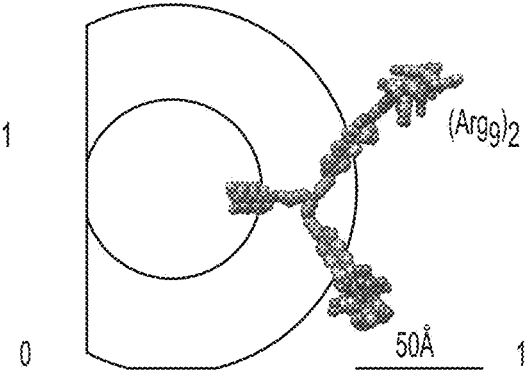
Figure 2C:
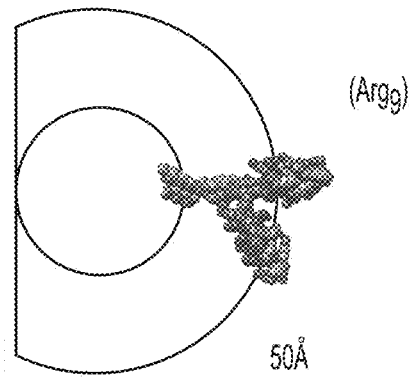
Figure 2D:
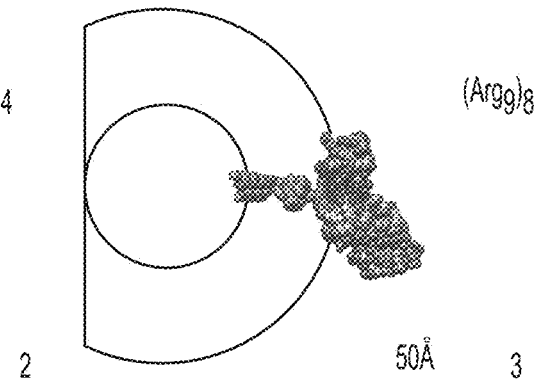
Figure 2E:
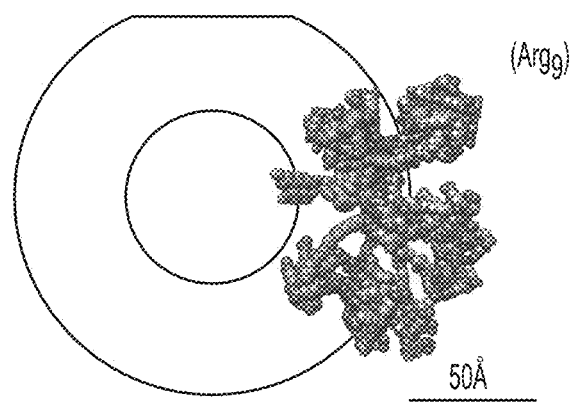

Prior to undertaking cellular delivery experiments, the peptides' ability to assemble to the QDs in a ratiometric manner and display their poly(Arg) residues on the QD periphery was verified. Estimates were made of the maximum number of each peptide species that would fit around and populate the QD surface during assembly; previous work has shown that the maximum number of small (<3 kDa) linear peptides that can assemble to these types of QDs is determined by the available number of binding sites on the QD surface. For the 4.7±0.4 nm diameter nanocrystals utilized here (representative TEM in FIG. 2A), this translates to ca. 50±10 linear peptides/QD. With increasing sizes of surface displayed moieties (i.e. proteins), the determining factor for QD population switches over to becoming dependent on steric or fitting constraints. The peptide series used in this work encompass linear peptides and large monodisperse peptidic dendrimers ranging from ~4 to 32 kDa in mass (Table 1). Three-dimensional structures of each of the peptides were assembled and docked to the QDs in silico. Because the His$_6$ tail coordinates to the Zn-surface, it is assumed not to contribute to the lateral extension of the peptide away from the QD surface. The Pro$_9$ segment is meant to act as a spacer that extends the peptides opposite terminus away from the QD surface. Due to their predominantly flexible and linear structure, especially within the predicted space occupied by the QDs surrounding PEG layer, the linear (Arg$_9$)$_1$ and bifurcated (Arg$_9$)$_2$ peptides both yield initial maximum assembly ratio estimates of ~41 per QD each. This is essentially just packing maxima based on the putatively available number of binding sites on the QD surface and not far from the 50±10 peptide maxima previously confirmed for assembly to a closely-sized QD species. Doubling the displayed poly(Arg) motifs from 2 to the (Arg$_9$)$_4$ structure reduces the packing number by 25% to 31. Estimated maxima of ~21 and ~11 are derived for assembly of the (Arg$_9$)$_8$ and (Arg$_9$)$_{16}$ structures, respectively. Overall, the doubling of displayed poly(Arg) motifs on the peptides produces a linearly decreasing progression from the linear/bifurcated peptides upwards if the (Arg$_9$)$_{1,2}$ are not differentiated from each other. There are only estimates since they do not take into account electrostatic interactions or repulsion between peptides nor their structural rearrangements when binding the QD surface and coming into contact with each other.

Figure 3A:
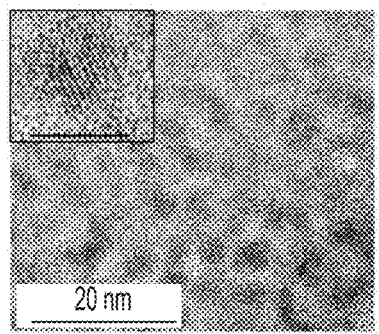
FIGS. 3A through 3E show the characterization of QD-(Arg$_9$)$_{1-16}$ conjugates.
Figure 3B:
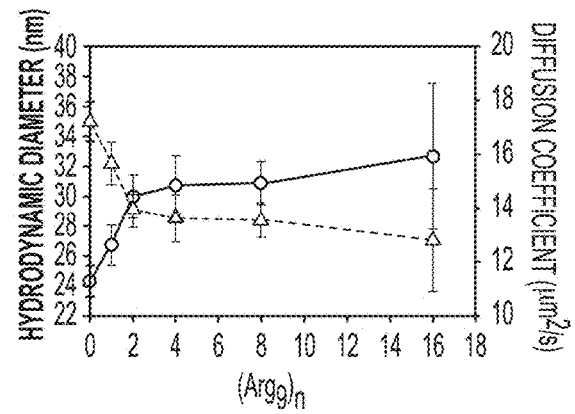

Dynamic Light Scattering (DLS) analysis was next undertaken to measure the QD-peptide conjugates hydrodynamic diameter (H$_D$) and diffusion coefficients. Based on the values estimated above, assembly ratios of 5 peptides/QD were utilized during these measurements. The results are shown in FIG. 3B and also partially listed in Table 1. The QD-(Arg$_9$)$_1$ conjugate's H$_D$ increases from the QD only value of 24.3±1 nm to ~26.7±1.3 nm. H$_D$ values for the QD-(Arg$_9$)$_{2-8}$ conjugates are essentially the same within experimental error with an average value of 30.5±0.5 nm while the QD-(Arg$_9$)$_{16}$ increases to ~33 nm. The diffusion coefficients follow the same trend but in an inverse manner from ~17 to 13 μm$^2$/s. These data correlate well with the modelled putative structures and earlier studies with linear QD peptides. They support the notion that the peptides are attached via the His$_6$ region to the QD surface and that the polyproline regions span through the PEG layer displaying the poly(Arg) motifs on the QD's surface through the surrounding PEG layer as intended in the synthetic design. Moreover, this structure does not dramatically increase the resulting conjugates overall H$_D$.

Figure 3C:
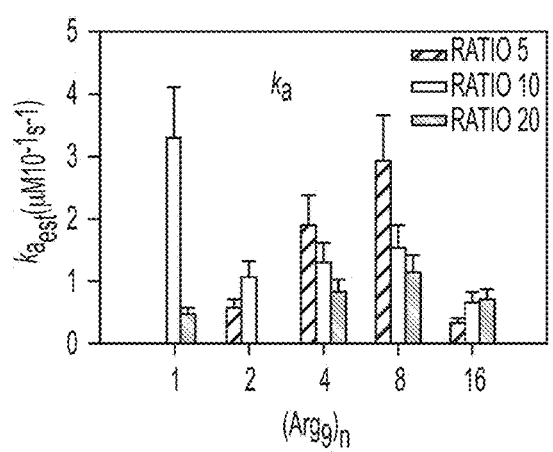
Figure 3D:
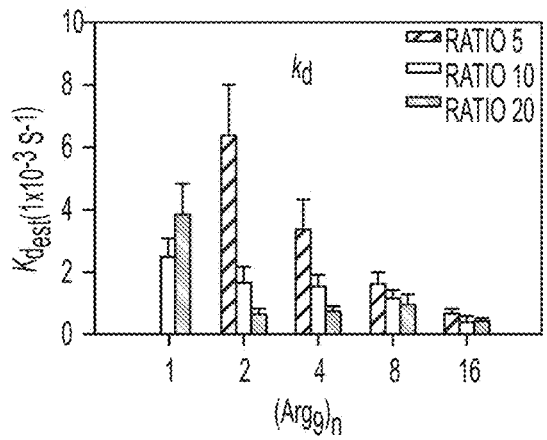
Figure 3E:
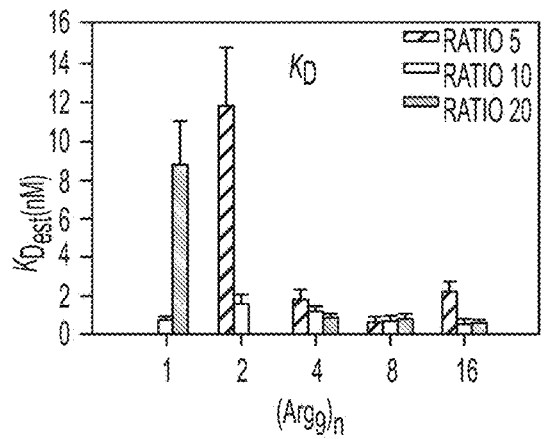
Figures 4A, 4B, 4C, 4D:
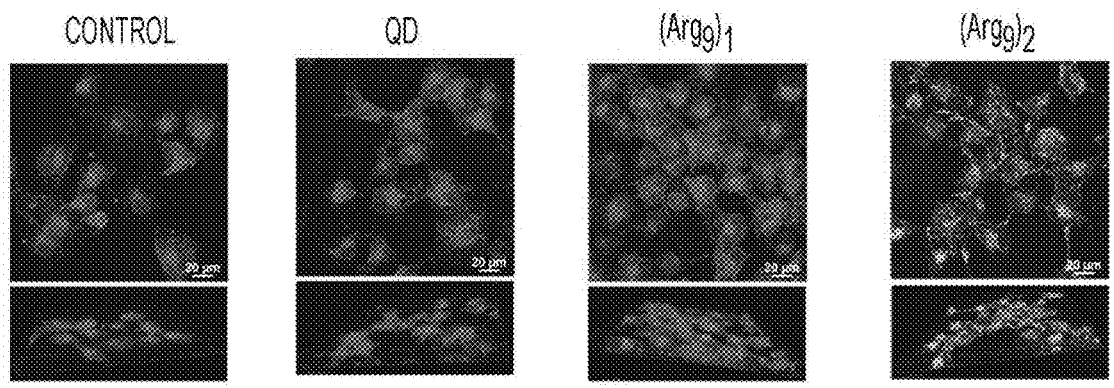
FIGS. 4A through 4G illustrate the initial uptake of QD dendritic peptide bioconjugates. Representative confocal micrographs of COS-1 cells exposed to QD-peptide conjugates. Images are shown as projections of confocal stacks and as side profiles of the cells. Cells were sequentially incubated with dendritic peptides-QD bioconjugates (5 peptides/QD) for 4 h and then the Transferrin-Alexa647 endosomal marker for 1 h. QD exposure concentration was 100 nM. Red fluorescence indicates endosomes labeled with Transferrin, green fluorescence the accumulation of 550 nm QDs, and blue the DAPI-labeled cellular nuclei. Strong colocalization (yellow) is seen between the Transferrin labeled endosomes and the QDs indicating that the dendritic peptide-QD conjugates are jointly located in endosomes. As the number of poly(Arg)$_9$ branches displayed increases, the overall green fluorescence increases, suggesting that the degree of QD uptake correlates with dendritic peptide branch number.
Figures 4E, 4F, 4G:
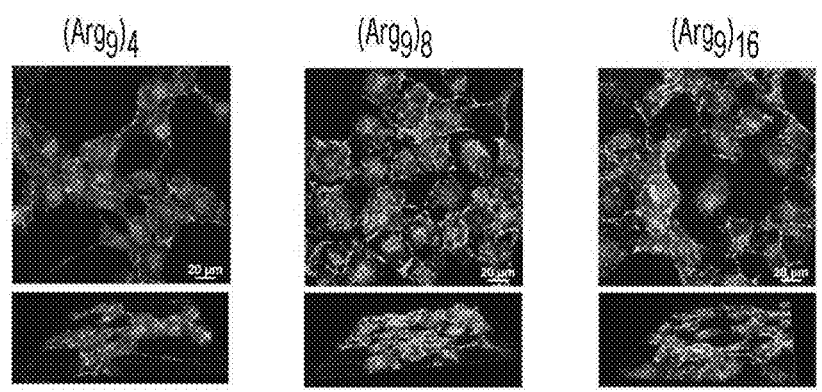

A surface plasmon resonance-(SPR) based binding assay was also used to evaluate the ability of the QD-peptide bioconjugate series to present the poly(Arg) motifs and bind to HSPG on coated assay chips meant to mimic the cellular membrane. Given the format of how these experiments were implemented, the kinetic values extracted from the experiments are estimates or apparent values and are only used for a semi-quantitative comparison. FIG. 3C plots the association rates, $k_a$, for each of the QD-(Arg$_9$)$_n$ conjugates at different assembly ratios (e.g. 5 peptides/QD=Ratio 5). The higher $k_a$ values indicate a rapid "on" rate or many successful interactions with the HSPG-coated chip surface. A trend of increasing values was observed for the QD-(Arg$_9$)$_{2-8}$ portion of the series and then a decrease is seen for the (Arg$_9$)$_{16}$, the latter may be due to steric hindrance. The dissociation rate, $k_d$, is used here to measure the stability of complex formation. A lower value reflects either a slower "off" rate or binding with high avidity. In FIG. 3D, the $k_d$ values decreases with increasing poly(Arg) display on the peptides indicating, as expected, that having a greater number of Arg residues available to interact with the HSPG would lead to a more stable or higher avidity binding/longer interactions. Although the QD-(Arg$_9$)$_{16}$ conjugates have lower association rates, possibly due to steric constraints, the $k_d$ results suggest that once it binds to the HSPG it achieves a remarkably stable interaction with very low off rates. The equilibrium dissociation constant $K_D$ is derived from the ratio of $k_d/k_a$ with lower values indicating higher affinity interactions. The plot in FIG. 3E shows the influence of increasing poly(Arg) display ratio on apparent $K_D$ values. For the QD-(Arg$_9$)$_{4-16}$ series, the low nM values suggest very strong binding and that low concentrations of dendritic peptide interact with the HSPG to form stable complexes. The anomalous results for the QD-(Arg$_9$)$_{1,2}$ conjugates may reflect the overall weaker interactions with the test surface. We also note a loose trend of better binding/avidity with increased ratio of peptide attached per QD as expected since this would also affect the number of potential binding interactions.

Initial Cellular Uptake of Quantum Dot-Poly(Arg)$_{1-16}$ Bioconjugates.

Preliminary experiments were performed to confirm that the poly(Arg)-based CPPs could indeed facilitate cellular uptake and delivery of QDs. The COS-1 cell-line was utilized as it has a long history of being applied for QD cellular delivery studies. In practice, nanoparticles might be delivered to living tissue in an animal such as a human.

COS-1 cells were incubated for 4 h with 150 µL of a 100 nM solution of QDs assembled with the (Arg$_9$)$_{1-16}$ peptide series at ratio of 5/QD. This ratio was chosen since it represents a value where stochastic assembly events are minimized and correlates with ratios used in the DLS and SPR analysis. Cells were then incubated with the Transferrin Alexa647 endosomal marker for another hour prior to washing and processing which included counterstaining with the DAPI nuclear dye as described in the Methods section. FIGS. 4A through 4G present representative micrographs collected from these samples as projections of confocal stacks and side profiles of the cells. Control samples not exposed to any QDs or peptide, QD only samples, and QDs assembled with the (Arg$_9$)$_1$ peptide show analogous results with strong nuclear and endosomal staining but no appreciable QD uptake. Significant QD uptake is noted for the remaining QD (Arg$_9$)$_{2-16}$ sample series with the most intense QD PL seen in the (Arg$_9$)$_{8,16}$ samples. The bright yellow PL also observed in these images reflects colocalization of the green QDs with the red Alexa647 marker and confirms that the QDs are located in the endolysosomal system with a primary perinuclear localization as expected following endosomal vesicular uptake.

Poly(Arg)$_{1-16}$-Mediated Quantum Dot Uptake as a Function of Time and Ratio.

Figure 5A:
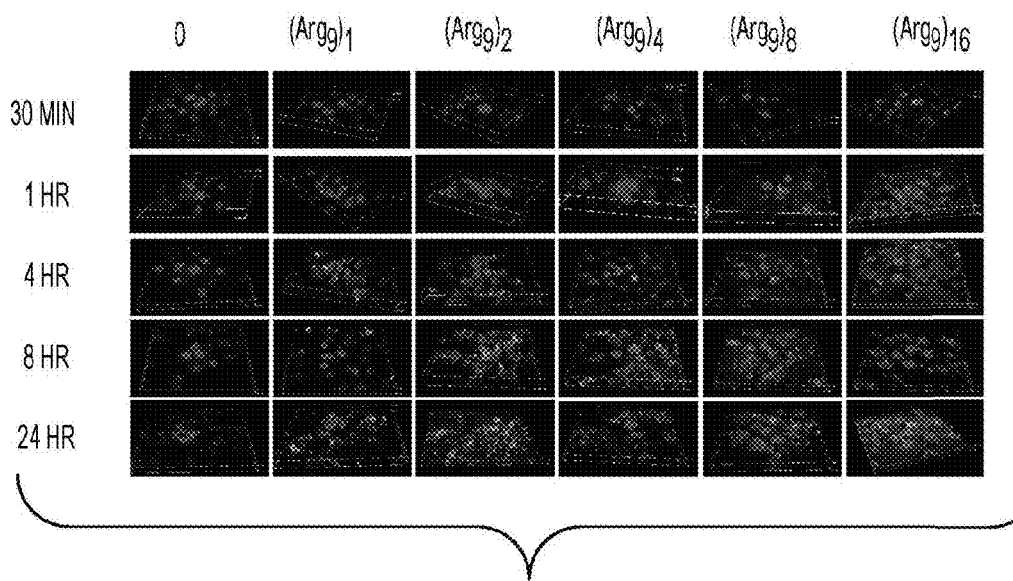
FIGS. 5A through 5C show that cellular uptake of QD-(Arg$_9$)$_{1-16}$ conjugates increases with (arg$_9$)$_n$ density and cellular exposure time.
Figure 5B:
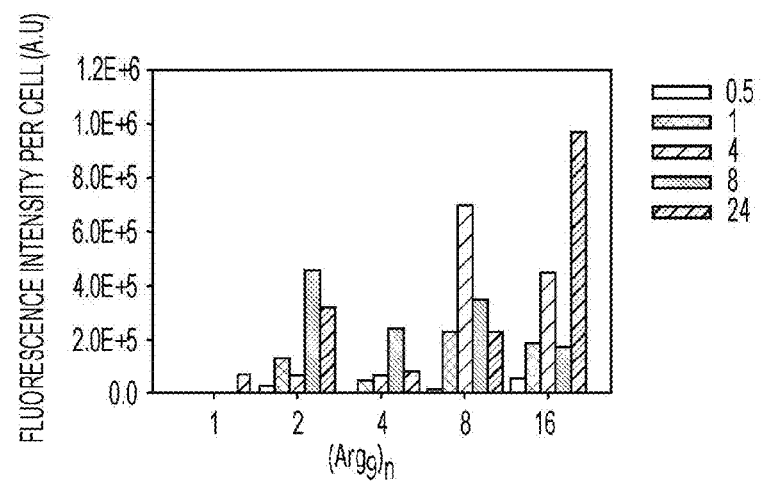
Figure 5C:
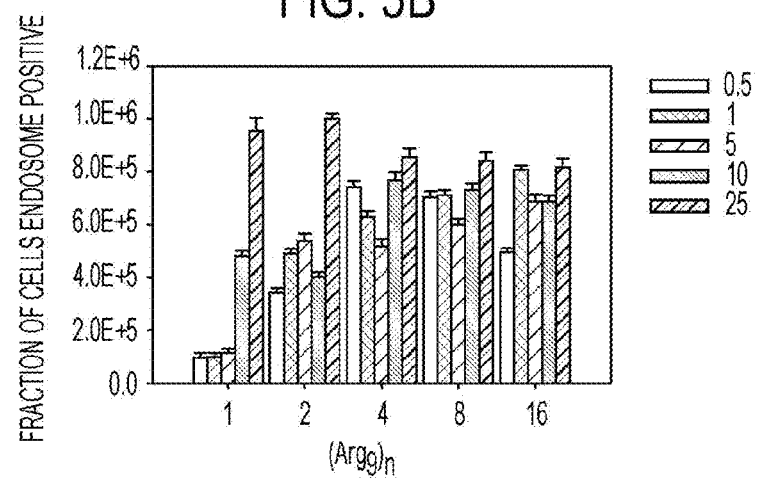

Kinetics of Poly(Arg)$_{1-16}$-mediated QD uptake into cells were next evaluated. For this, 150 µL of 100 nM QDs assembled with a ratio of 5 peptides/QD were exposed to COS-1 cells for fixed time periods of 0.5, 1, 4, 8 and 24 h. FIG. 5A displays representative confocal projection images of these cells following washing, fixing and counterstaining with DAPI nuclear dye. Some delivery trends are visible from a comparison across these images. At the earliest 30 min time point, distinct punctate labeling can be observed for the QD-(Arg$_9$)$_2$ samples but not for the QD-(Arg$_9$)$_1$ samples. The amount and brightness of QD labeling in the endosomes directly correlates with the increase in the dendritic poly(Arg) display on the QD surface. Additionally, as the cellular exposure time increases, the amount of QD uptake increases proportionally as well. The measured PL intensity per cell from these representative images is plotted in FIG. 5B highlighting the general trends. Although some variability was noted (most likely due to the inherent noisy background found in such gross cellular studies), replicate samples reproduced the same generalized trends of increased poly(Arg)$_n$ dendritic branching and increased cellular exposure time leading to increased bioconjugate uptake and PL intensity. For the (Arg$_9$)$_{16}$ samples, some nonspecific attachment of QDs to the growth matrix on the bottom of the chamber especially at the later time points was observed. This was not unexpected given that each of these peptides has 144 Arg residues present (×5 peptides per QD=720 Arg); this should translate into a similar number of positive charges potentially displayed around the QD, see Table 1. We also noted some QD uptake for the QD-only sample at later time points; this, too, is not unexpected given the long incubation times with cells and has been observed previously. The observed PL for the QD only sample is insignificant at <8 h. Similarly, the uptake for the QD-(Arg$_9$)$_1$ sample is also extremely low and below scale across the same time period in comparison to the results of the (Arg$_9$)$_{2-16}$ samples FIG. 5C shows data collected from these experiments where the fraction of cells displaying QD-stained endosomes is quantified as a function of increasing poly(Arg) density on the peptide as well as ratio of peptide/QDs for a 1 h cell exposure time. Similar trends are readily apparent here as well. Cellular delivery efficiency directly depends upon both poly(Arg) branching and the subsequent peptide ratio/QD implemented. The uptake efficiency plateaus when poly(Arg) display density per peptide reaches 4. The QD-(Arg$_9$)$_{16}$ samples again display extremely efficient uptake even at the lowest ratios, similar to that described above.

Figure 6A:
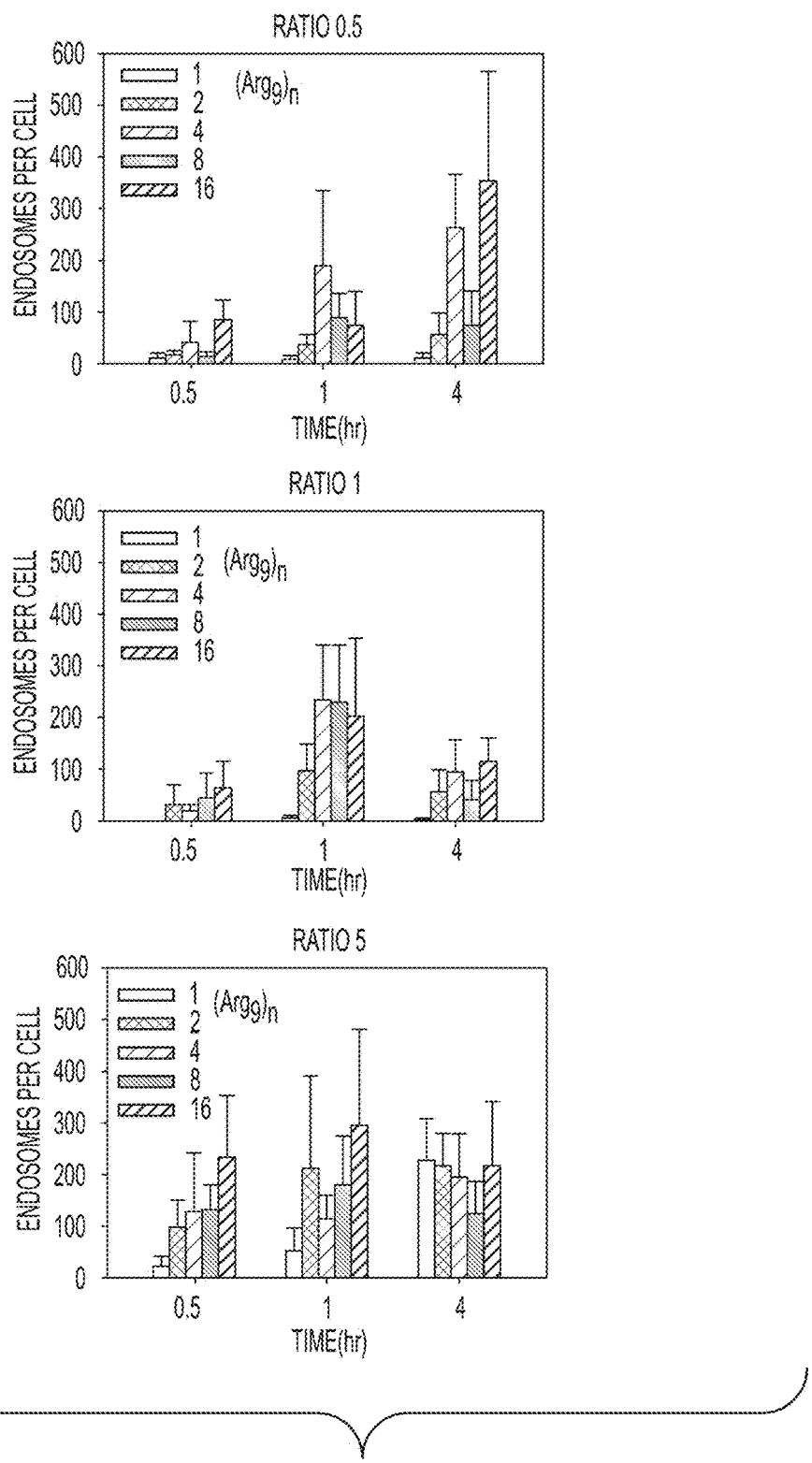
FIGS. 6A through 6C illustrate QD uptake as a function of time and peptide ratio. QD cellular uptake for each of the peptides was monitored at ratios of 0.5, 1, and 5 peptides per QD for cellular exposure times of 0.5, 1 and 4 h. Intervening points are excluded from these plots to simplify the overall data presentation. Data were analyzed using the Metamorph Granularity module.
Figure 6B:
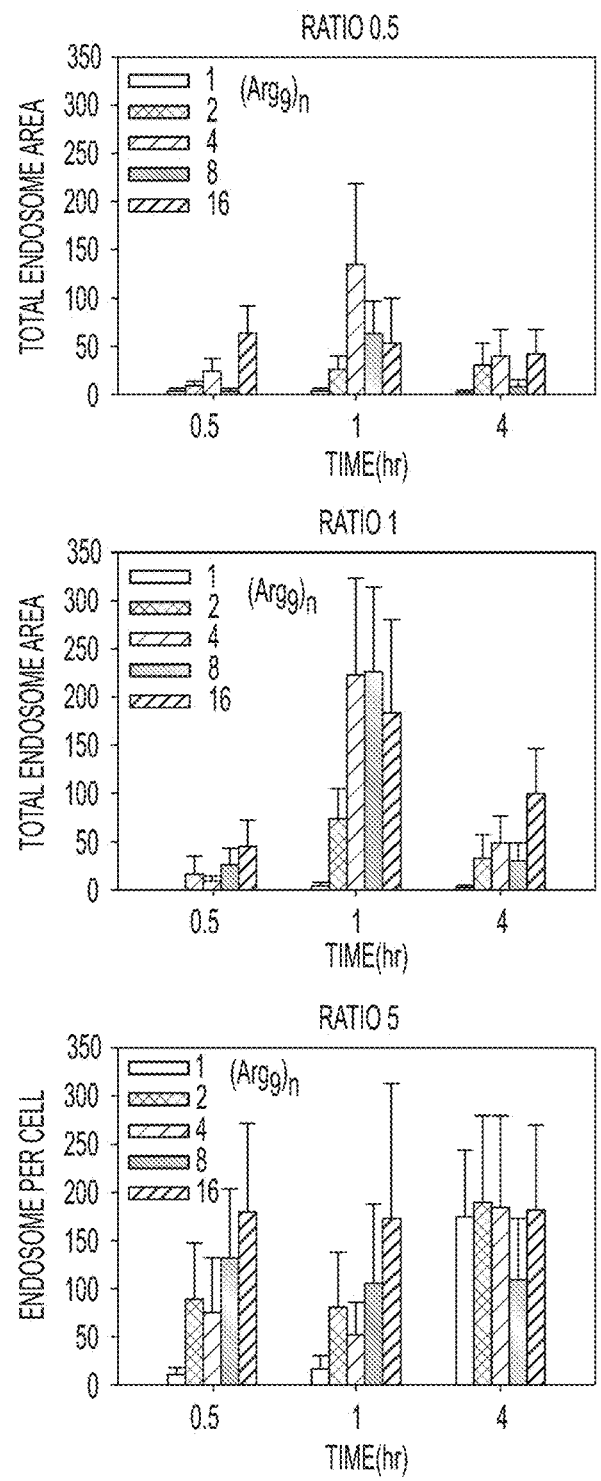
Figure 6C:
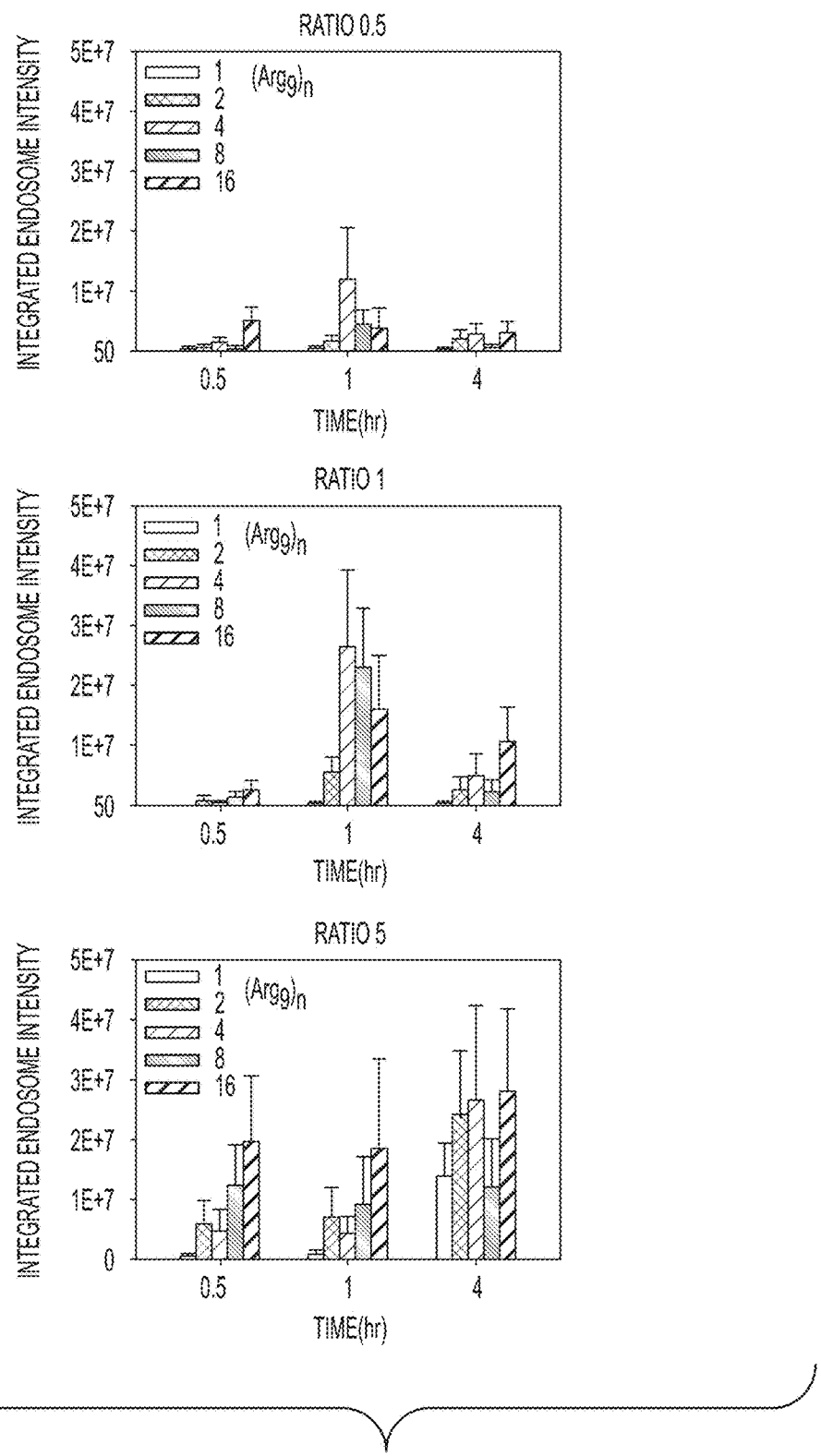
Figure 7A:
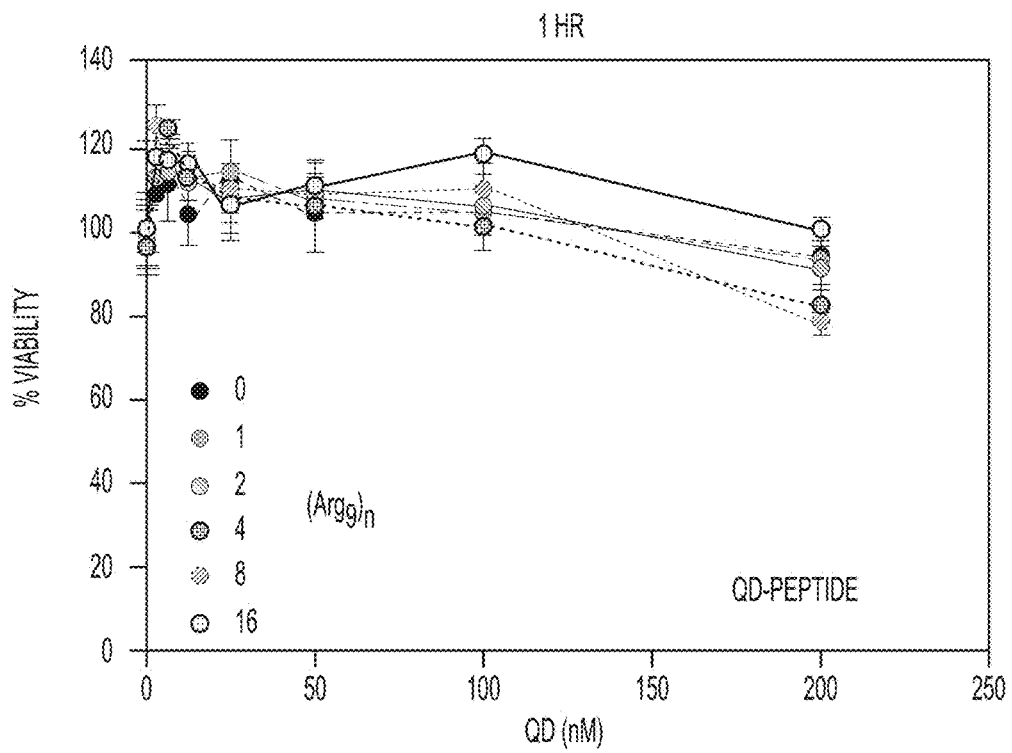
FIGS. 7A through 7D shows results of cellular toxicity assays. Proliferation of COS-1 cells was measured by the MTT assay after 1 h (FIGS. 7A and 7B) or 24 h (FIGS. 7C and 7D) exposure to increasing concentrations of QD-peptide conjugates assembled at a ratio of 5 peptides/QDs or the equivalent concentration of dendritic peptide alone. QD concentration was varied over a range from 3 to 200 nM and dendritic peptide concentration concomitantly from 15 to 1000 nM.
Figure 7B:
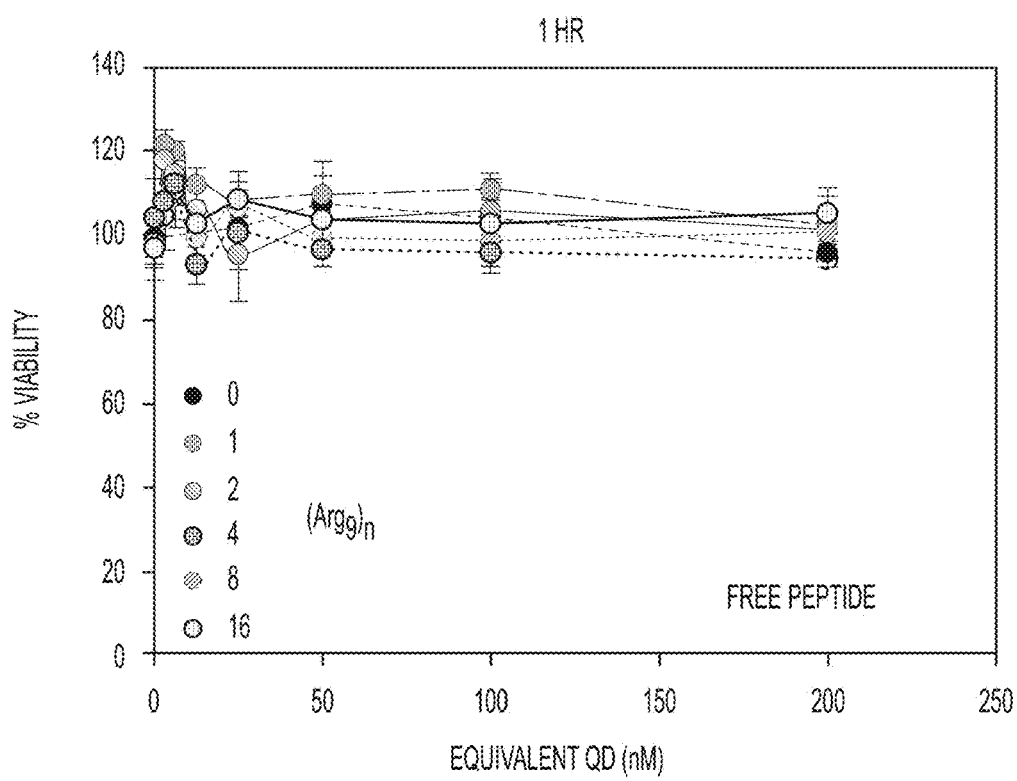
Figure 7C:
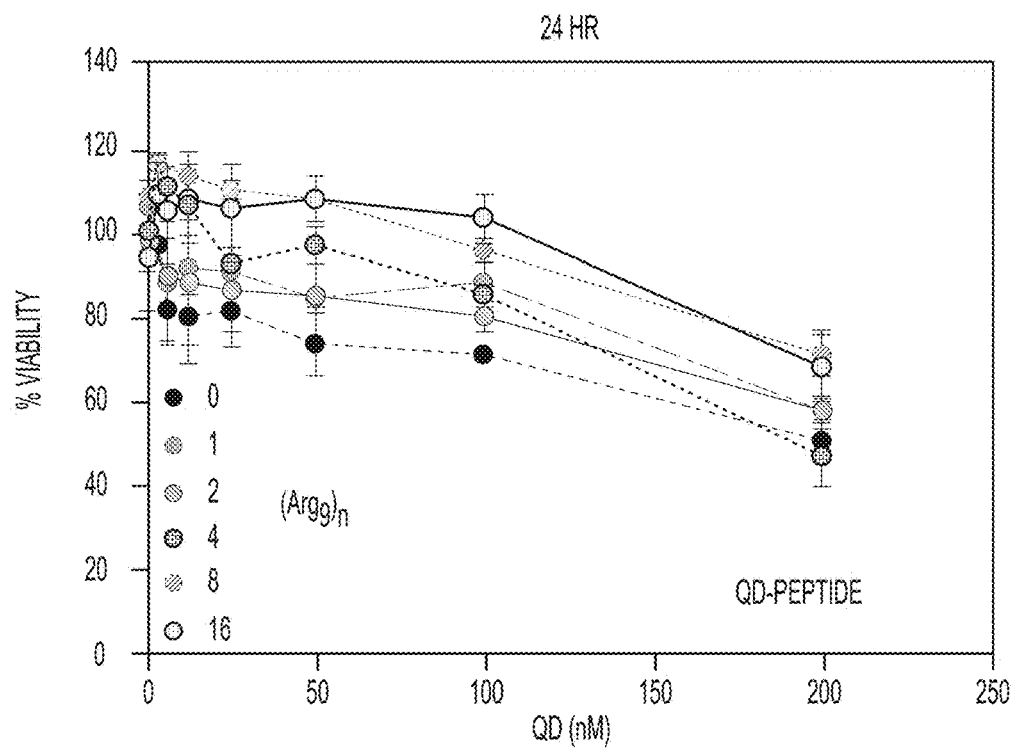
Figure 7D:
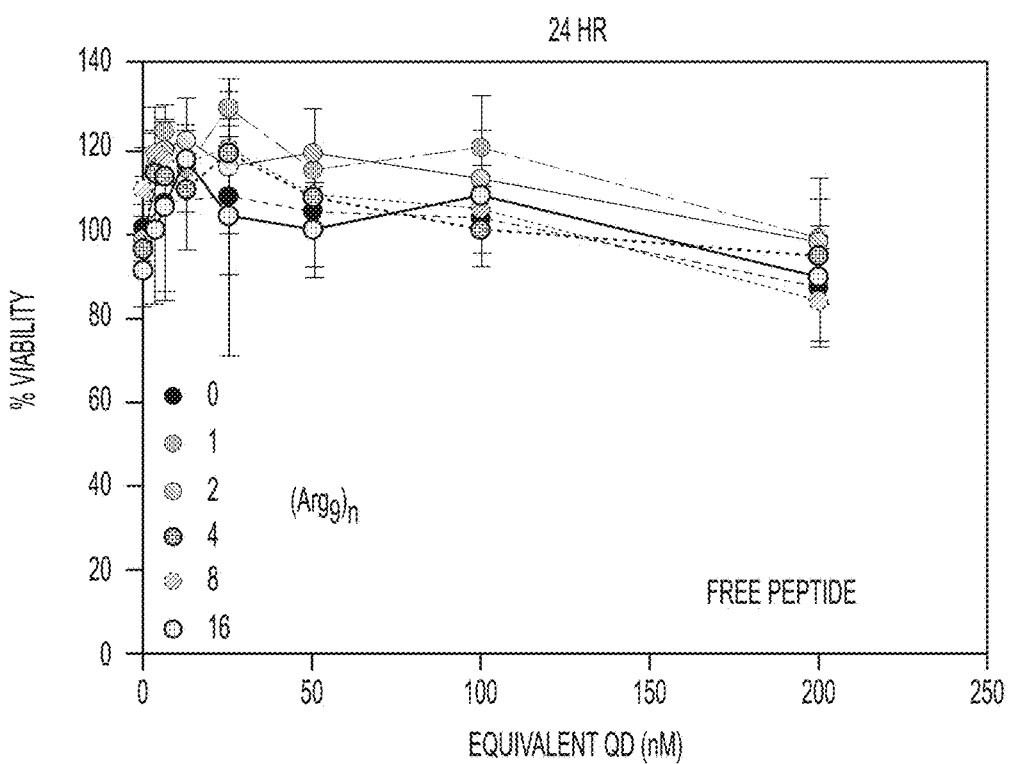

Since much of the above data indicates that most uptake occurs at or before 4 h and at a ratio of 5 peptides/QD or less, measuring were made of some of the kinetics occurring within this time and ratio window in a semi-quantitative and comparative manner. Following on the data highlighted in FIG. 5C, the average number of endosomes per cell demonstrating QD labeling were quantified using the Olympus Metamorph Granularity software module. FIG. 6A plots these data for each of the peptides for ratios of 0.5, 1, and 5 peptides/QD at time points of 0.5, 1 and 4 h. Clearly, the number of QD containing endosomes per cell increases as a function of both time and ratio in a manner that is proportional to poly(Arg) display density per peptide. Interestingly, the average value appears to plateau at around 300-400 endosomes per cell which could perhaps reflect the putative total number of endosomes present on average in this cell-line. Figure +B utilizes the same format but plots the total endosomal area which is collected as a function of the green PL with a punctate appearance within each cell; this, in essence, reflects the total amount of QD material being taken up per cell. FIG. 6C plots the integrated endosomal intensity reflecting the amount of QD material present per endosome. Cumulatively, this analysis suggests that not only does the number of QD positive cells increase based on poly(Arg) display density, ratio of peptide, and exposure time, but the number of QD positive endosomes and the amount of QD material accumulating within the endosomes increases as well.

Figure 1B:
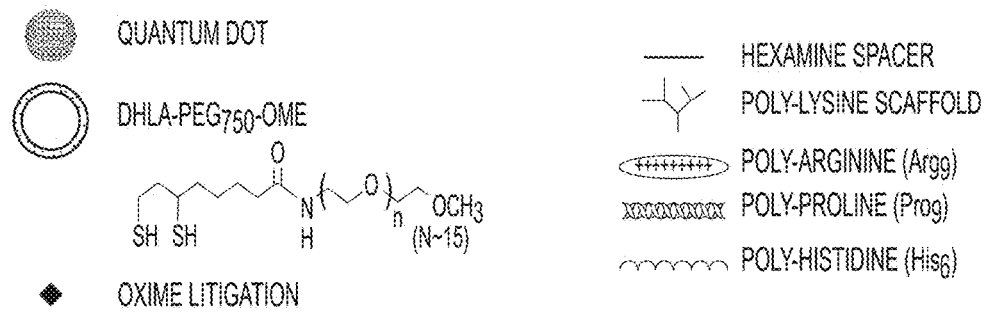
Figure 1B:
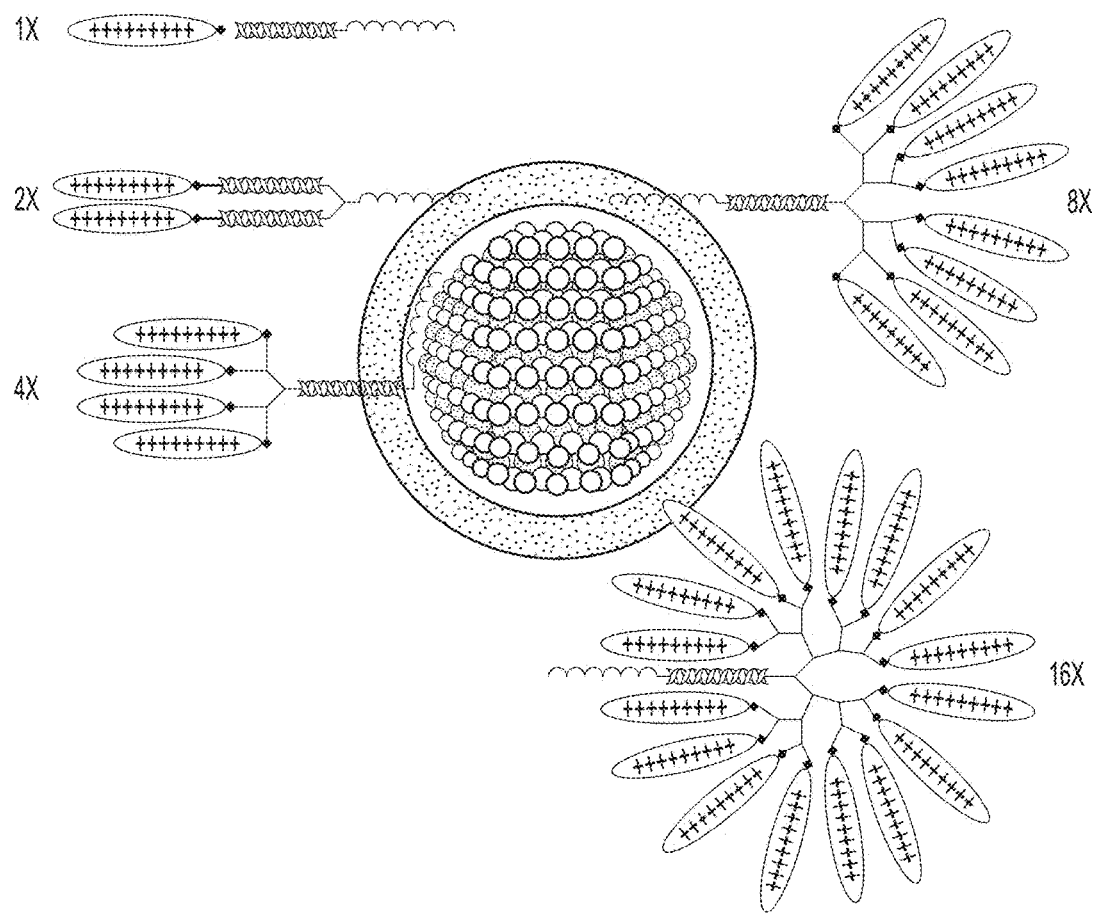

Cellular Toxicity Assays. Standard MTT, 3-(4,5-dimethylthiazol-2-yl)-2,5-diphenyltetrazolium bromide, cytoviability assays were performed to determine if any significant cytotoxicity was associated with the free dendritic poly$(Arg_9)_{1-16}$ peptides along with the QD-$(Arg_9)_{1-16}$ bioconjugates. Ratios of 5 ligands/QD were used and COS-1 cells were exposed to serially-diluted samples starting at a concentration of 200 nM of $(Arg_9)_{1-16}$-QD or the equivalent amount of ligand without QD present for either 1 or 24 h. FIGS. 7A-7D present representative results from these assays. After 1 h delivery and at the typical exposure concentration of 100 nM used for most of the current studies, the QD samples yielded a cell viability of ~100%. At the higher 200 nM concentration, cell viability was over 80%, irrespective of the dendritic poly(Arg) branching. For the equivalent amounts of free peptide with the same 1 h exposure, there was no measureable cytotoxic effect based on concentration or dendritic poly(Arg) branching. Only at high ratios of 25 peptide to QD and with the longer incubation time (24 hr) did we see any appreciable cellular toxicity (Supplemental FIG. 1). For both time points in the data shown, the dendritic peptides were no more cytotoxic than exposure to the same concentration of QDs alone.

Monovalent Peptide Delivery of QDs and QD-Cargo Conjugates.

Figure 8A:
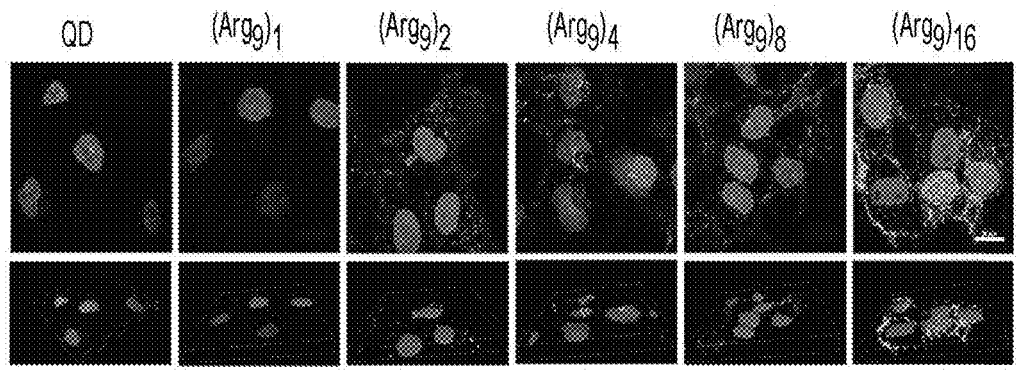
FIGS. 8A and 8B shows single dendritic peptide QD delivery and cargo delivery. For FIG. 8A, QDs were assembled with a ratio of 0.5 peptides per QD, providing for 2 species in the ensemble: unlabeled QDs and those with monovalent display of peptide. COS-1 cells were incubated with 100 nM dendritic peptide-QDs for 30 min and then washed, processed and imaged. Micrographs are shown as projections of confocal stacks and as side profiles of the cells. The results show effective QD delivery starting with the $(Arg_9)_2$ construct and increasing in a manner that tracks increasing poly(Arg) display per peptide.

With the ultimate goal of achieving single peptide delivery of QDs (and other future nanoparticulate materials) to cells in a rapid manner, focused assays were conducted to confirm if this was indeed possible. For these experiments, QDs were assembled at a ratio of 0.5 peptides/QD which, as described earlier, provides for 2 QD species in the ensemble sample; those that are unlabeled and those assembled with a single copy of a given peptide (1:1). COS-1 cells were then exposed to 150 µL of a 100 nM concentration of each QD conjugate. FIG. 8A shows representative micrographs collected from the cells following a 30 min exposure to the QD conjugates. QD PL is clearly visible for the QD-$(Arg_9)_{2,4,8,16}$ samples with the QD-$(Arg_9)_{16}$ sample again yielding the most intense PL comparatively. No appreciable QD PL is detected in the QD only and QD-$(Arg_9)_1$ samples. For the QD-labeled samples, the QD PL appears as a mix of membranous staining and punctate intracellular staining suggesting that some conjugates have already achieved endosomal uptake to the cytosol while others are still at the initial stages of uptake and vesicular formation at the membrane. This result was not unexpected given the very brief cellular exposure time prior to imaging. Longer exposure times with the same samples resulted in uptake of more QD material into cells and more of it being intracellularly located in endosomes (data not shown). Nevertheless, these results unequivocally confirm that the dendritic peptides are capable of achieving QD delivery with only a single dendritic poly$(Arg_9)$ peptide attached per QD. This capability starts at the first generation structure displaying the bivalent $(Arg_9)_2$ motif but is not observed with the monovalent QD-$(Arg_9)$ suggesting the latter is incapable of achieving this, at least under these experimental conditions.

Figure 8B:
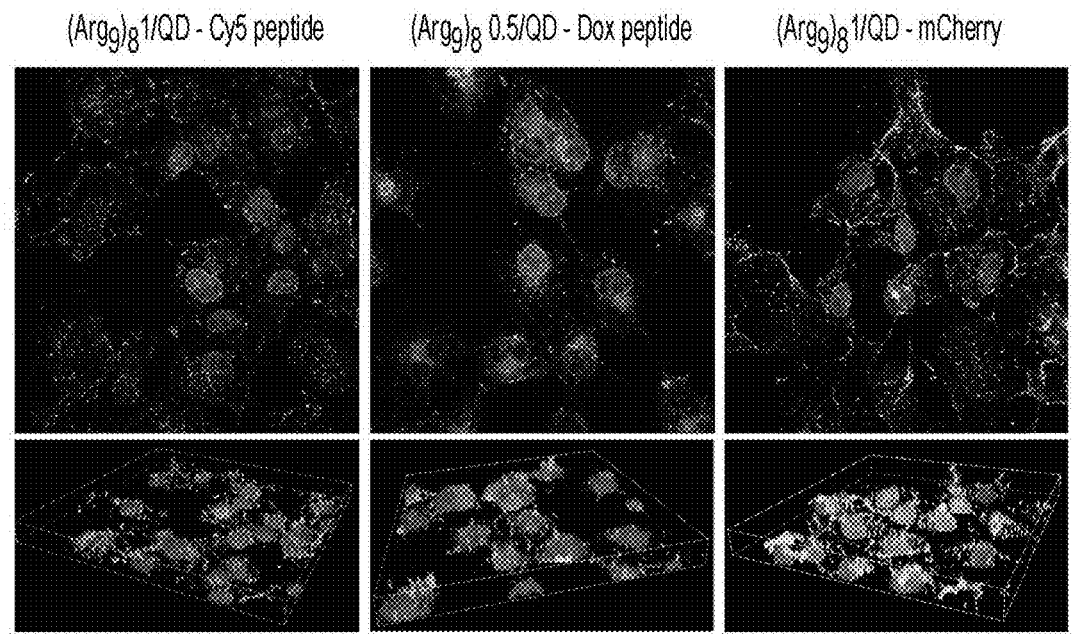

Lastly, as proof of concept, tests were made of the ability of the dendritic peptides to facilitate QD delivery, when the QDs are decorated with additional "cargo." For this, following initial attachment of the $(Arg_9)_n$ peptides to the QDs, they were further assembled with one of three prototypical cargos, a dye-labeled peptide, a drug-labeled peptide and a fluorescent protein. FIG. 8B presents a series of representative images that highlight some of the results achieved using 520 nm emitting QDs functionalized with a zwitterionic compact ligand 4; this ligand was used as it still allows larger proteins access to the QD surface for $(His)_n$-binding unlike PEG which can sterically preclude them. These images show that a ratio of 1 $(Arg_9)_8$/QD facilitated delivery of QDs decorated with ~30 Cy5 labeled peptides (total cargo MW ~100 kDa/QD) using a 2 h exposure. A ratio of 0.5 $(Arg_9)_8$/QD allowed delivery of QDs decorated with ~25 doxorubicin labeled peptides (cargo MW ~50 kDa) using a 1 h exposure, and 1 $(Arg_9)_8$/QD allowed delivery of ~30 mCherry per QD (cargo MW ~850 kDa) with a 1 h exposure of the conjugates to the cells. Analogous to the data shown above, peptides with higher $(Arg_9)_n$ dendrimeric branching, use of higher ratios of peptide/QD, and longer delivery times each served to facilitate higher levels of QD-cargo conjugate uptake into the cells (data not shown). Overall, these results show that single copies of dendritic peptides can also facilitate efficient delivery of cargo-display QDs. They also confirm that delivery can be extended to a different QD sample functionalized with a different surface ligand and with a substantial amount of cargo equal to or even larger in size than the dendritic peptides displayed around each QD.

In view of this success in delivering this wide variety of cargoes, it is expected this similar approaches (such as conjugating the cargo to a polyhistidine-bearing peptide that can attach to a nanoparticle) could be used to deliver diverse cargos to cells.

Discussion

The three-dimensional architecture inherently provided by dendrimers, including especially the ability to sequentially double terminal moiety display as a function of generation number, naturally lends itself to polyvalent display. Numerous examples from the literature abound here as well. For example, the Holl group showed that folate display on dendrimeric scaffold greatly enhanced binding to the bovine folate binding protein. Similar results were obtained with methotrexate display on a generation 5 polyamidoamine (PAMAM) dendrimer also targeting folate binding protein. Kwok and colleagues showed that a peptide dendrimer/lipid hybrid could improve DNA transfection efficiency by 6-10 fold over commercial reagents. Angeles-Boza et al., attached up to 6 TAT peptides to a scaffold peptide in pursuit of a delivery vehicle with better endosomolytic properties. In terms of multi-TAT peptide based display, some important design criteria can also be gleaned from previous work. Dendrimeric-structures may be better suited for such polyvalent displays as attaching multiple copies of nona-Arg peptides to a linear scaffold was associated with a higher level of cytotoxicity. It is also important for the binding moiety to extend out sufficiently from any surrounding PEG layer on a NP in order to assure the appropriate initial binding occurs with a cell surface and does not experience electrostatic, steric or other types of repulsion.

Here the approach was to test the cell penetrating proficiency of increasing dendritic display numbers of the $Arg_9$ TAT motif contained within a single peptide entity displayed on the surface of NPs in pursuit of improving intracellular cargo delivery and achieving stoichiometric NP delivery. The poly$(Arg_9)_{1-16}$ ligand series was efficiently assembled via oxime ligation of the $Arg_9$ TAT membrane binding motif modified with nucleophilic amino-oxy groups to the QD binding core scaffolds equipped with aldehyde groups. Oxime ligation was chosen due to its chemoselective and quantitative reaction characteristics. The peptide dendrimer assembly protocol requires a minimal number of synthetic steps, thus representing an elegant assembly strategy that is broadly applicable for the synthesis of a diverse range of peptide dendrimers. This approach furthermore overcomes a significant hurdle in the potential therapeutic use of dendrimers, as it enables the production of protein-like monodisperse dendrimers, which complies with a regulatory requirements for single entities (not polydisperse). The peptide series utilized here incorporates several design criteria to meet key functional necessities along with simplifying the required assembly chemistry. An initial $H_6G_2P_9W$ (SEQ ID No: 3) "starter peptide" was synthesized along with the $GFR_9$ membrane binding segment. To ensure that the poly(Arg) segments were accessible to the cell surface, the $P_9$ motif was added to the starter peptide to extend this portion beyond the QD's surrounding PEG layer. For increasing the number of nona-Arg presented in the peptides, a series of increasing lysine dendrimeric generations were extended from the W on the starter peptide. These were then coupled to the nona-Arg segment using oxime ligation. The only deviation from this design is the $(Arg_9)_2$ peptide which was assembled with slight modifications as described in the Methods. This convergent synthetic strategy ensured an elegant and efficient ligand assembly of the otherwise quite complex and difficult to synthesize peptide dendrimers (i.e. the 4×, 8×, 16× peptide dendrimers could not be synthesized in linear SPPS fashion). Within this series, the monovalent and linear $(Arg_9)_1$ mimics other TAT-based CPPs and functions as a control reflecting their activity. Moreover, the sequence used is nearly identical to the TAT-based CPP we have utilized with QDs and other NPs previously.

Prior to the cellular uptake experiments, peptide assembly to the QDs was both confirmed and characterized. The upper assembly limit or maximum display capacity of peptide per QD was estimated using structural simulations. As expected, for the smaller $(Arg_9)_{1,2}$ peptides, the determining factor was the number of available $His_6$ coordination sites on the QD surface while for the larger $(Arg_9)_{4,8,16}$ peptides steric fitting constraints determined their maxima given their increasing mass. These simulations, in conjunction with the DLS results suggest that the peptides are indeed displayed around the QDs but that the poly(Arg) termini do not extend out from the PEG surface more than 5-8 nm. SPR based binding assays confirmed that once attached to the QDs, the peptides facilitate binding to HSPG in a manner where binding affinity correlates to the number of $(Arg_9)_n$ displayed on a given construct. Preliminary experiments utilizing a ratio of 5 peptides/QD confirmed that the $(Arg_9)_n$ peptides can facilitate cellular uptake by endocytosis and that the QD conjugates remain in the endolysosomal system. Previous results have shown that peptides attached to QDs by the same metal affinity coordination remain attached to the QDs for at least 4 days following endosomal uptake into cells. Moreover, such QD-TAT peptide constructs largely remain in the endosomes unless other escape peptides or endoosmolytic chemicals are simultaneously utilized.

The influence of increasing the dendritic $(Arg)_n$ display within a peptide, peptide/QD ratio, and incubation time on cellular uptake of QDs were then compared in side-by-side cellular uptake assays. Here, the cumulative results consistently reflect the same overall trends, namely, the number of QD positive cells and the amount of QD material delivered increases in a manner that correlates directly to increases in the dendritic branching of the $(Arg)_n$ units, peptide/QD ratio, and exposure time. These results also clearly illustrate that QD delivery can be very efficient with short exposure times of 0.5 to 4 h along with eliciting minimal to no concomitant cytotoxicity from the cells. Critically, the $(Arg_9)_{2-16}$ peptide dendrimers are able to accomplish the goal of single peptide delivery of QDs to cells in a rapid manner (FIGS. 8A and 8B). Single peptide delivery of QDs conjugated to significant amounts of peptide (~100 kDa), drug (~25 copies) and protein (~850 kDa) cargo is equally feasible. Moreover, dense display of repeated copies of such variable cargoes do not appear to disrupt the peptides ability to facilitate this type of delivery. This certainly bodes well for incorporation into multifunctional theranostic nanodevices displaying repeated copies of various other cargo materials.

From these results one can extrapolate a functional set of rules, at least for using these peptides to deliver QDs to cells, and these should also form a good starting basis for delivering other types of NPs to cells. For the exposure dosages utilized here, typically exposing cells to 150 µL of 100 nM QD-peptide conjugate, the minimal poly(Arg) density needed is at least 2 branches, $(Arg_9)_2$, with the $(Arg_9)_{4,8}$, working very effectively and the $(Arg_9)_{16}$ representing perhaps overkill. Although single peptide delivery is clearly feasible, utilizing ratios of 2 to 5 peptides per QD may be more effective as this will ensure that almost all the QDs in a given sample have at least one or more peptides displayed on their surface. Delivery times of 1-4 hr also appear to work best with less time needed as the density of poly(Arg) on a peptide increases. Choice between using the $(Arg_9)_{2,4,8}$ peptides versus the $(Arg_9)_{16}$ construct represents, for all intents and purposes, a cost-benefit decision. Clearly, the latter peptide should facilitate the highest cellular membrane binding avidity along with the most rapid and efficient uptake kinetics at the lowest ratios per QD. However, this would be at the cost of taking up more space on the QD surface along with the possibility of non-specific interactions given the large number and high localized density of positive charges from the Arg residues. Supporting this, it was found that the $(Arg_9)_8$ peptide worked best at low valencies with short delivery times for the cargo delivery experiments (data not shown). Although not tested here, these same peptides should be similarly functional for facilitating delivery of a wide array of NP materials from hard metals to softer polymers, similar to what has been shown when using the typical TAT motif. The current peptide sequences will attach to any NP material displaying a $Ni^{2+}$-nitrilotriacetic acid (NTA) group while synthesis of thiolated versions can allow conjugation to gold and other noble metal NPs.

The actual mechanism by which this peptide series potentiates QD delivery to cells is intriguing. Most simplistically, the higher the binding affinity of a given peptide for the cell membrane, the greater the amount that should bind in a more rapid timeframe and then stay bound as well. Thus, the increasing number of Arg residues present could bind to more HSPG and in a tighter and longer manner. However, comparing between the results in FIG. 5 for the $(Arg_9)_1$ and (Arg$_9$)$_2$ peptides at the 0.5 and 1 h time indicates that the bifurcated peptide is far more efficient than the monovalent construct even when the latter is present on the QD at a greater ratio. This suggests that the bivalent peptide has a potentiated effect. Even though it is only a simulation, the corresponding structure for this peptide in FIG. 1 suggests that the 2-nona-Arg motifs would be well separated especially given their charge repulsion. This brings up the possibility of the same peptide binding to multiple receptors on the cell membrane which can result in receptor crosslinking, a phenomenon known to trigger endocytic uptake into cells. Indeed, this very mechanism has been previously observed when crosslinking acetylcholine receptors on muscle cells with bungarotoxin attached to QDs. This may explain why higher ratios of monovalent TAT CPPs are required, in general, to effect efficient QD uptake into cells. Previous work has also shown that His$_6$-appended peptides tend to assemble to QDs in a very random manner that would preclude localized bunching. Enhanced uptake by the 1 (Arg$_9$)$_{4,8,16}$ peptides may represent a combination of both avidity effects and receptor crosslinking. These mechanisms are, of course, just speculative at this point as they require specialized materials and experimental formats that are far beyond the current scope.

These results confirm that a single peptidyl entity can efficiently facilitate cellular uptake of a NP. This will allow for other functional molecular species to be attached to the NP surface and increase their net capabilities or cargo carrying capacity. Such high avidity peptides may also be useful as direct drug or contrast agent delivery vehicles on their own. Although single-peptide facilitated cellular uptake represents only a single step in the journey that a NP-drug conjugate may take through a patient's body, the same high avidity approach may be extendable to other entities attached to the NP surface such as, for example, tumor targeting peptides or similarly functional molecular ligands (e.g., folate). This could, in turn, provide further capacity to the NP. It is also important to keep in mind that most such NP materials are colloids meaning that they are stabilized and held suspended in solution by their surface ligands. Minimizing the amount of extraneous materials directly attached to such colloids will certainly help minimize perturbations to their long-term stability. This outlook is, of course, tempered by the reality that far, far more needs to be done before NMDD and theranostics become an everyday reality. As stated earlier, pursuing these goals are certainly providing fertile avenues of research.

Materials and Methods

Dendritic Peptide Synthesis. A detailed description is provided in the Supporting Information appendix. Dendrimer peptide purification was carried out using centrifugal size-exclusion membrane filters and peptides were quantified by measuring the Trp absorbance at 280 nm. Peptides were desalted, dried down and stored at −20° C. until needed as described. Prior to use, peptides were typically solubilized in DMSO (less than 5% final volume) and then diluted to 10 μM working concentration in 1× phosphate buffered saline (137 mM NaCl, 10 mM phosphate, 2.7 mM KCl, pH 7.4, PBS).

Quantum Dots.

CdSe/ZnS core/shell QDs with emission maxima centered at 550 nm were synthesized as described. These were rendered hydrophilic through cap exchange of the native hydrophobic ligands with polyethylene glycol-(average MW 750 Da) appended dihydrolipoic acid ligands terminating in methoxy groups (DHLA-PEG$_{750}$-OMe, see FIG. 1B) as described. For cargo delivery experiments, 520 nm emitting QDs functionalized with a zwitterionic compact ligand 4 (CL4) were utilized.

Dynamic Light Scattering Analysis.

Dynamic light scattering (DLS) measurements were carried out using a ZetaSizer NanoSeries equipped with a HeNe laser source (λ=633 nm, Malvern Instruments Ltd, Worcestershire, UK) and analyzed using Dispersion Technology Software (DTS, Malvern Instruments Ltd). 50 nM concentration solutions of QDs were loaded into disposable cells, and data were collected at 25° C. All samples were prepared in 0.1×PBS buffer pH 7.4. For each sample, the autocorrelation function was the average of five runs of 10 s each and then repeated from three to six times. CONTIN analysis was used to determine the number versus hydrodynamic size profiles for the dispersions studied.

Surface Plasmon Resonance Binding Analysis.

SPR experiments were performed using the ProteOn™ XPR36 protein interaction array system. This instrument allows the binding of six analytes to six ligands to be evaluated simultaneously. Heparin sulfate proteoglycan (HSPG) was purchased from Sigma. First, the HSPG was biotinylated to facilitate immobilization to the surface of a sensor chip. 100 μL HSPG (0.4 mg/mL) as supplied was dialyzed versus three changes of PBS. Then the HSPG was biotinylated using 10× sulfo-NHS-LC-LC-biotin (Life Technologies). Excess biotin (Bt) was removed from the Bt-HSPG by gel filtration with Zebra™ Spin Desalting Columns, 7K MWCO, 0.5 mL (Thermo Scientific). An NLC Sensor Chip (Bio-Rad) compatible with the ProteOn™ was utilized for the SPR assays, since it comes prepared with NeutrAvidin bound to the GLC polymer layer with a binding capacity of approximately one protein monolayer. Dilutions of the Bt-HSPG (~25, 8, and 3 μg/mL) were flowed for 5 minutes at 30 μL/min over three of the six channels of an NLC sensor chip. The Bt-HSPG NLC chip was then turned 90 degrees to evaluate the binding of the various QD-peptide preparations (ratio 5/QD) along with their off-rate versus buffer. Relative values and slopes of the signal collected during binding and flow versus concentration were utilized to estimate kinetic parameters, including the association and dissociation rates ($k_{on}$ and $k_{off}$) and apparent binding constant ($K_D$) in a manner similar to that described previously. Given the constraints of this experimental format, we qualify all values as apparent or estimated only and they are primarily used for comparative purposes.

Model of Quantum Dot-Dendritic Peptide Bioconjugates.

Structures of the dendritic peptides were simulated using tools in UCSF Chimera (version 1.4.1). Structures were assembled from three basic components: a poly-arginine segment, a linker consisting of either lysine of hexylamine, and a binding segment with a poly-proline spacer. The His$_6$, G$_2$ and other portions were adapted from previous models. The bonds joining the components were also assembled in Chimera. Sequences are summarized in Table 1. Energy minimization was carried using built in features including ANTECHAMBER (version 1.27) and the AM1-BCC method of calculating charges. After assembly, torsion angles were adjusted to correct for inappropriate contacts. The assembled peptides were placed on the surface of a QD with a radius of ~23.5 Å surrounded by a shell representing the 33 Å thick layer of PEG on the QD surface. To estimate maximum peptide loading on the QD (surface area 6939 Å$^2$), the contact area of the peptides His$_6$ binding region (167 Å$^2$), the surface of the PEG layer (40,115 Å$^2$), and where the peptide(s) reach their maximum diameter in shape as placed on the QD surface (and contact each other) all need to be considered. For the peptides containing only one or two (Arg$_9$) helices, the maxima is predicted to be ~41 peptides/QD reflecting the number of available binding sites on the QD surface rather than any steric interference between peptides. For the higher branched dendrimers, it is the space occupied by the branched structures that limits peptide loading. Thus, taking the size and shape of the dendrimer along with distance from the surface results in maximum loading of ~31, 21, and 11 peptides per QD for the (Arg$_9$)$_{4,8,16}$ dendrimers, respectively.

Self-Assembly of Quantum Dot-Dendritic Peptide Bioconjugates.

His$_6$-appended dendritic peptides were conjugated to the surface of 550 nm CdSe/ZnS QDs capped with DHLA-PEG$_{750}$-OMe ligands using metal affinity based coordination. The indicated molar ratios of peptide/QD, typically from 0.5 up to 5 peptides/QD (or sometimes higher as indicated), were added to the QDs in 25 mM 4-(2-hdroxyehyl)-1-piperazineethanesulfonic acid (HEPES) and 1 mM sodium pyruvate. Final QD concentration was 100 nM QD and the bioconjugates were incubated at room temperature for approximately 30 min to ensure complete assembly.

Cell Culture and Quantum Dot Delivery.

Aliquots of African green monkey kidney fibroblast-like COS-1 cells (CRL-1650) from American Type Culture Collection (ATCC, Manassas, Va., USA) were cultured in Dulbecco's Modified Eagle's Medium (DMEM, ATCC) supplemented with 10% (v/v) heat-inactivated fetal bovine serum (ATCC) and 1% antibiotic/antimycotic at 37° C. in a humidified atmosphere containing 95% air/5% CO$_2$. Aliquots were allowed to adhere to the culture flask and reach 80% confluency, usually within 3 to 4 days. The monolayer was harvested by washing once with PBS, once with calcium/magnesium-free PBS, and incubating the monolayer with trypsin until detachment from the culture flask (usually within 5 min). Cells were seeded at 1-2×10$^4$ cells/well in Lab-Tek 8-well chambered No. 1 borosilicate cover glass system (Nalge Nunc, Rochester N.Y., USA) that had been previously coated for at least 4 h with fibronectin (5 µg/mL, Life Technologies). Cells were allowed to adhere to the bottom of the wells by further culture overnight at 37° C. in 95% air/5% CO$_2$ air. Following overnight culture, media was removed and washed with 100 µL of 25 mM HEPES supplemented with 1 mM sodium pyruvate. This was replaced with 150 µL of 100 nM QD-peptide bioconjugates at the ratios indicated and cells were incubated at 37° C. for at least 30 min up to 24 h. For endosomal labeling, the cells were subsequently incubated with transferrin-Alexa647 in HEPES for 1 h. For cellular imaging, the supernatant containing QDs or Alexa647 was removed, the cells washed twice with PBS, fixed with 3.8% paraformaldehyde in PBS for 20 min, and the nuclei stained with 1 µg/mL 4',6-diamidino-2-phenylindole (DAPI) dye for 10 min. Cell samples were stored in PBS with 0.5% sodium azide and wrapped in foil at 4° C. until analysis.

For cargo delivery experiments, mCherry fluorescent protein was prepared as described in the literature. The peptide HHHHHHSLGAAAGSG-[Hyz]-KSSTGGQNGEDTGTSC*CONH$_2$ (Hyz=hydrazine bond, CONH$_2$=amide blocking the C-terminal carboxyl) (SEQ ID No: 4) was assembled as described from commercially synthesized starting peptides (BioSynthesis, Lewisville, Tex.), labeled on the cysteine-thiol with Cy5-maleimide dye and purified as described. GSGAAAGLSHHHHHH-CONH$_2$ (SEQ ID No: 5) was conjugated to doxorubicin on the N-terminal amine using the crosslinker bis(sulfosuccinimidyl)suberate (BS3) and purified with HPLC. Cytotoxicity assays were determined using the Vybrant® MTT Cell Proliferation Assay Kit. COS-1 cells were seeded into 96-well plates at 5×10$^3$ cells per well and allowed to adhere overnight. Cells were exposed to serially diluted solutions of either 5 or 25 peptides per QD or the equivalent amount of free peptide in solution for 1 or 24 h. Peptide and mCherry cargo were assembled to QDs as above following attachment of the dendritic peptide.

Cellular Imaging.

Cellular imaging was performed using bright field and epifluorescence microscopy with an Olympus IX-71 total internal reflection fluorescence microscope equipped with a 60× oil immersion lens. For each time point and ratio of peptide to QD analyzed, experiments were performed in at least triplicate cell cultures and then a minimum of 20 fields of view were collected for each fluorescent color or stain. These were then merged and analyzed in Metamorph using the "Granularity" software module where applicable. For each data point within the plots presented here, the data reflects analysis from 80-100 individual cells collected from duplicate to triplicate experiments along with the standard deviation where applicable. Confocal imaging was performed using a Nikon A1Rsi or a Nikon C1 microscope and analyzed with NIS Elements.

Advantages and New Features

This technique provides several advantages and new features:

(1) Ability to synthesize dendritic wedge peptides ranging in display of the (Arg$_9$)n binding motif with n=1×, 2×, 4×, 8×, 16× multivalency (2) Ability to achieve NP cellular uptake with single dendritic peptide with as few as two (Arg$_9$) branches after a short incubation period of 30 minutes (3) Ability to deliver >600 kDa protein cargo per NP to cells with only one dendritic wedge peptide and an incubation time of 1 hr (4) Simplistic synthetic assembly strategy (5) Synthesis of monodisperse peptide-like dendrimers (6) Polyproline region extends dendrimer away from NP surface, ensures poly(Arg) segments are available to bind to cell surface (7) Use of lysine to create increasing dendrimer generations (8) Biocompatibility (9) Small, molecular weight

(10) Compact arrangement of branched cell penetrating peptides yielding more surface area on the NP for cargo attachment.

(11) High affinity for QD/NP surfaces due to His$_6$

(12) High affinity and applicability to other nanoparticle materials (Au, Ag, Cu, Pt, Pd)

(13) High affinity for cell membranes due to localized Arg residues

(14) Ability to synthesize dendritic wedge peptide with different chemical handle

(15) Ability to synthesize dendritic wedge peptide with more than one chemical handle

(16) Stable at biologic pH
(17) Modular design

CONCLUDING REMARKS

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. A method of delivering a nanoparticle to a cell comprising:
    contacting a living cell with a nanoparticle bound to a single dendritic peptide thereby causing entry of the nanoparticle into the cell,
    wherein the dendritic peptide comprises a polyhisitidine motif and a hinge and a spacer connecting the polyhistidine to a lysine-based dendritic wedge displaying at least two copies of the peptide sequence RRRRRRRRRFG (SEQ ID No: 2).

2. The method of claim 1, wherein the nanoparticle is also bound to a cargo which is delivered to the cell with the nanoparticle.

3. A method of delivering a nanoparticle to a cell comprising:
    contacting a living cell with a nanoparticle bound to a single dendritic peptide thereby causing entry of the nanoparticle into the cell,
    wherein the dendritic peptide comprises a hexahistidine motif connected to a lysine-based dendritic wedge displaying at least two copies of the peptide sequence RRRRRRRRRFG (SEQ ID No: 2) via a hinge and spacer comprising six prolines and two glycines.

4. The method of claim 3, wherein the nanoparticle is also bound to a cargo which is delivered to the cell with the nanoparticle.

5. A method of delivering a nanoparticle to a cell comprising:
    contacting a living cell with a nanoparticle bound to a single dendritic peptide thereby causing entry of the nanoparticle into the cell
    wherein the dendritic peptide comprises a polyhisitidine motif and a hinge and a spacer connecting the polyhistidine to a lysine-based dendritic wedge displaying at least two copies of the peptide sequence RRRRRRRRRFG (SEQ ID No: 2); and
    wherein the nanoparticle is free of any other cell-penetrating peptides.

6. The method of claim 5, wherein the nanoparticle is also bound to a cargo which is delivered to the cell with the nanoparticle.

* * * * *